United States Patent [19]

Katz et al.

[11] 4,440,601
[45] Apr. 3, 1984

[54] METHOD AND APPARATUS FOR HIGH VOLUME FRACTIONAL DISTILLATION OF LIQUIDS

[76] Inventors: Jerome Katz; Sidney J. Fogel, both of Rochester, County of Monroe, N.Y.

[21] Appl. No.: 224,072

[22] Filed: Jan. 15, 1981

Related U.S. Application Data

[63] Continuation-in-part of Ser. No. 115,615, Jan. 28, 1980, abandoned, which is a continuation-in-part of Ser. No. 769,291, Feb. 22, 1977, Pat. No. 4,186,060, and a continuation-in-part of Ser. No. 787,832, Apr. 18, 1977, Pat. No. 4,186,058.

[51] Int. Cl.³ ............. B01D 1/28; B01D 3/14; B01J 8/02
[52] U.S. Cl. ............. 203/24; 422/129; 585/649; 585/651; 585/709; 203/19; 203/26; 203/91; 203/94; 203/98; 203/100; 203/DIG. 6; 203/DIG. 13; 203/DIG. 20; 203/DIG. 24; 202/153; 202/233; 202/180; 202/182; 202/205; 60/649; 208/108
[58] Field of Search ............. 203/19, DIG. 13, 10, 203/11, DIG. 6, DIG. 8, 26, DIG. 14, 24, 100, DIG. 24, 28, 29, 91, 94, 98, 88; 202/205, 182, 172, 173, 235, 234, 174, 233, 180, 153, 158, 162, 160; 435/161, 93, 813; 426/11–16, 494, 493; 568/916; 422/187, 129; 585/649–651, 709; 208/108; 60/648, 649

[56] References Cited

U.S. PATENT DOCUMENTS

| 63,116 | 3/1867 | Tait et al. ............. 435/161 |
| 2,826,601 | 3/1958 | Barsky ............. 203/DIG. 6 |
| 3,423,293 | 1/1969 | Holden ............. 203/26 |
| 3,598,607 | 8/1971 | Morse et al. ............. 426/11 |
| 3,671,404 | 6/1972 | Meckler ............. 203/DIG. 6 |
| 4,009,075 | 2/1977 | Hoge ............. 435/165 |
| 4,035,243 | 7/1977 | Katz et al. ............. 203/DIG. 14 |
| 4,194,964 | 3/1980 | Chen et al. ............. 203/DIG. 6 |
| 4,215,011 | 7/1980 | Smith ............. 203/DIG. 6 |

Primary Examiner—Wilbur L. Bascomb, Jr.
Attorney, Agent, or Firm—Sixbey, Friedman & Leedom

[57] ABSTRACT

A method and apparatus for high volume distillation of impure liquid, particularly of binary mixtures of relatively low boiling organic substances and water, comprises fractionally distilling the impure liquid to form a vapor of a low boiling organic substance; compressing the vapor; passing at least a portion of the compressed vapor through a vapor composition adjustment zone wherein the organic substance may catalytically or otherwise react or merely stabilize following compression; compressing the vapor exiting the adjustment zone to form a recompressed vapor; cooling the recompressed vapor in heat transfer relation with the impure liquid whereby the vapor at least partially condenses, transferring sufficient heat to the impure liquid for evaporating the liquid and to form the aforementioned low boiling organic vapor; and collecting the condensed low boiling organic vapor. In various embodiments of the invention the vapor exiting the adjustment zone may be expanded through an expansion engine and/or a portion of the compressed vapor may bypass the adjustment zone and/or the expansion engine and admix with the remainder of the vapor passing through the adjustment zone and/or expansion engine. Work may be added to the expansion engine by mechanical means, such as motor means, drivingly linked to the engine, by admixing hot gases directly with the compressed vapor passing through the expansion engine, by a combination of direct mechanical drive and direct mixing of hot gases, or by other suitable means.

The method and apparatus are particularly suitable for producing substantially anhydrous ethyl alcohol.

86 Claims, 16 Drawing Figures

METHOD AND APPARATUS FOR HIGH VOLUME FRACTIONAL DISTILLATION OF LIQUIDS

This application is a continuation-in-part of copending application Ser. No. 115,615, filed Jan. 28, 1980, now abandoned, which application was a continuation-in-part of Ser. No. 769,291, filed Feb. 22, 1977, now U.S. Pat. No. 4,186,060, and of application Ser. No. 787,832, filed Apr. 18, 1977, now U.S. Pat. No. 4,186,058.

The present invention relates to a method and apparatus for economically and efficiently separating and recovering high quality organic and inorganic components contained in aqueous and non-aqueous solutions and mixtures and, more particularly, to a method and apparatus which permits evaporation and vapor compression treatment of large volumes of impure water, as defined herein.

The need for treating very large volumes of high quality water has arisen in recent years in many contexts. Many industries require large quantities of good quality water as input or raw material in order to operate. For example, the paper or textile industries utilize tremendous volumes of such water for their dyeing and bleaching operations. Many more industries discharge large quantities of waste or contaminated aqueous solutions to the environment. However, with the continuing decline in quality of the water in our lakes, rivers and streams and the continuing promulgation by federal, state and local governments of statutes and ordinances regulating the quality of water dumped into waterways, there has been an increasing need for economical methods by which industrial waste streams can be cleaned prior to discharge. Another area which requires the treating of large volumes of water in an efficient and economical fashion is the production of potable water from the oceans by desalination. A related area for treating large volumes of water is the treatment of sea water into which oil has been spilled to recover the oil and to desalinate or purify the water. Thus, the problem of waste water treatment in high volumes includes the treatment of impure water as well as sea or brackish water. It also includes the treatment of water containing inorganic or organic materials. Many of the problems associated with purifying and recovering large volumes of water have been dealt with by applicants in U.S. Pat. Nos. 4,035,243, 4,186,058 and 4,186,060. These patents disclose vapor compression methods and systems which, although applicable to the separation and recovery of the inorganic or organic materials in the water, focus on the recovery of pure water. Other patents which teach or disclose water distillation and/or vapor compression systems are the following: U.S. Pat. Nos. 1,230,417; 1,594,957; 2,280,093; 2,515,013; 2,537,259; 2,589,406; 2,637,684; 3,412,558; 3,423,293; 3,425,914; 3,351,537; 3,440,147; 3,444,049; 3,476,654; 3,477,918; 3,505,171; 3,597,328; 3,477,918; 3,505,171; 3,597,328; 3,607,553; 3,649,469; 3,856,631; 3,879,266.

In many instances where it is desired to separate water from an inorganic or organic material therein, recovery of the water is only of secondary interest. Of primary concern is separation and recovery of the inorganic or organic material, frequently in substantially anhydrous form. A typical illustration is the separation of water and ethyl alcohol from binary mixtures thereof in order to recover the ethyl alcohol in a form suitable for admixture with gasoline to form the currently popular gasoline substitute known as gasohol. The ethanol recovered must be anhydrous in order to prevent component separation in the fuel tank prior to use.

Ethyl alcohol and water form an azeotrope at atmospheric pressure which contains 95.6% by weight EtOH and boils at 78.15° C. If the ethyl alcohol is to be used as a primary fuel then the 95.6% azeotrope can be used. However if the EtOH is to be mixed with gasoline to form gasohol, then the EtOH must be anhydrous. There have been endless suggestions for treating EtOH-$H_2O$ mixtures to remove the water and to recover substantially anhydrous EtOH. For example, benzene or other well known hydrocarbons suitable for the purpose may be added to the mixture to form a tenary azeotrope which carries over the water as a distillate leaving the anhydrous EtOH behind as the bottom. Alternatively, counter-current extraction with a third component such as glycerine or ethylene glycol may be used. The third component depresses the vapor pressure of the water and allows anhydrous EtOH to be distilled from the top of the extraction column. The problem with these methods, however, is that benzene, glycerine and ethylene glycol, and their equivalents useful in the separation of anhydrous EtOH, are commercially derived from petrochemicals and, as petroleum becomes increasingly scarce, the production of EtOH by these methods becomes increasingly costly. On the other hand, methods which employ relatively abundant and inexpensive raw materials are unable to concentrate the EtOH beyond 95.6% and resort must eventually be had to the aforementioned petrochemical methods to prepare anhydrous EtOH. Thus typical fermentation or enzymatic conversion processes applied to sugar or hexose containing carbohydrate produces a "beer" containing 6–12% by weight EtOH, carbon dioxide, water, fusel oils, and aldehydes. This "beer" is vented to recover carbon dioxide and distilled to separate the low boilers, such as EtOH, aldehydes and fusel oil, from the residue, known as slop or stillage. Both the carbon dioxide and slop have valuable uses. The low boilers are condensed to a 50-60% EtOH solution and passed to a fractional distillation column where the aldehydes and other low boilers are separated as the overhead fraction, most of the EtOH is separated as the middle fraction, and the tails containing some EtOH are removed as the bottom fraction and recycled. The EtOH-containing middle fraction is further refined in a fractionating column which yields 95.6% EtOH as one of the products.

Any system or method heretofore suggested which is capable of treating the millions of gallons per day of EtOH-water mixtures necessary to effectively deal with anticipated "gasohol" needs or to even produce meaningful quantities of anhydrous EtOH has been hopelessly impractical or uneconomical in terms of their capital equipment, energy, extensive processing and/or scarce raw materials (e.g., petrochemicals) requirements. This is true not only for separation and recovery of EtOH from EtOH-water binary mixtures but also for separation and recovery of most valuable organic materials from aqueous or non-aqueous solvents where the materials can be substantially separated by the method of distillation. Exemplary of such other combinations which present separation problems of the nature encountered with EtOH-$H_2O$ mixtures are crude oil and water, crude oil bottoms, shale oil, solvents, e.g., methyl-ethyl ketone and water, and the like. Therefore, all possible feed solutions for separation of one fractionally distillable component from other constituents of the solution, whether the solvent is aqueous or not, are encompassed within the term "impure liquid" as used herein.

It is therefore an object of this invention to provide an economical yet practical fractional distillation system for high volume purification to impure liquid sources.

It is another object of this invention to provide a thermo-mechanical distillation system capable of purifying large volumes of impure liquids and recovering valuable organic or inorganic components without imposing unreasonable equipment or energy requirements.

It is yet another object of this invention to provide a thermo-mechanical distillation system capable of reacting the organic or inorganic components separated from the impure liquids to convert such components to more valuable forms.

It is a more particular object of the invention to provide a fractional distillation, vapor compression, heat and work input system capable of recovering substantially anhydrous EtOH from relatively dilute EtOH-water systems wherein maximum heat and work input efficiencies are practiced.

It is still another object of the invention to provide a method and means for producing and harvesting a raw material from which substantially anhydrous EtOH can be economically recovered without reliance upon petrochemicals.

Other objects and advantages will become apparent from the following description and appended claims.

Briefly stated, in accordance with the aforesaid objects one broad aspect of the present invention comprises a method, and a system for practicing the method, for purifying large volumes of impure liquid by fractionally distilling the liquid in an evaporator, preferably under partial vacuum, to separate the liquid at least into high boiling and low boiling fractions, substantially adiabatically compressing the resulting vapor (comprising the low boiling fraction) in a first compressor to a pressure substantially in excess of the vaporization pressure, directing at least a portion of the compressed vapor through a vapor composition adjustment zone in which the vapor may be vented, reacted or otherwise altered in composition, compressing the vapor exiting the adjustment zone in a second compressor to form a recompressed vapor and passing the resulting recompressed vapor through a condenser, such as the condenser side of the evaporator, wherein the recompressed vapor will, upon condensing, give up thermal energy to vaporize the feed liquid. The first compressor is preferably driven by linking it to an auxiliary turbine which may itself be driven by passing a volume of hot gas, e.g., combustion gas, steam, etc., therethrough. In one embodiment, the auxiliary turbine blading is annularly disposed with respect to the compressed vapor flow path and is driven by combustion gases produced in the annular space. Alternatively, the first compressor may derive at least a portion of its power from motor means shaft linked directly thereto. The second compressor may be driven in the same manner as the first compressor or in any suitable way. In an optional form of the system at least a portion of the compressed vapor may be processed by substantially adiabatically expanding the vapor in an expansion engine and adding sufficient make-up work to the expansion engine such that the added work plus the work done by the compressed vapor passing therethrough at least equals the work done by the compressor on the vapor. The work added to the turbine can be added by directly mixing the compressed vapor, under substantially isobaric conditions, with a volume of hot, clean gas, e.g., combustion gas, or by directly driving the turbine e.g. with an externally powered engine, by a combination of direct mixing and direct driving, or by other means well known in the art.

According to this method, maximum utilization is made of available thermal energies with the result that more efficient and economical high volume separation of fractions can be accomplished than with any other method heretofore known. Moreover, the system of the present invention, particularly when used to separate and recover anhydrous EtOH from EtOH-water solutions, is extremely flexible in terms of its utility.

The invention will be better understood from the following description considered together with the accompanying drawings, wherein like numerals designate like components, in which.

The invention will be better understood and appreciated from a consideration of a preferred embodiment thereof which, for purposes of a descriptive clarity, includes only a single effect fractional distillation. It is of course appreciated, as is well known in the art, that multi-effect distillation and other evaporative systems have many efficiencies which recommend them in practical usage. The present invention contemplates the use of multi- as well as single-effect evaporative units. In addition, the invention contemplates both vacuum and flash evaporation as well as any other known evaporative techniques for producing high volumes of vapor at $P_1$, $T_1$, as will more clearly appear hereinafter. It is, however, preferred to use vacuum evaporation or vacuum distillation.

Figure 1:
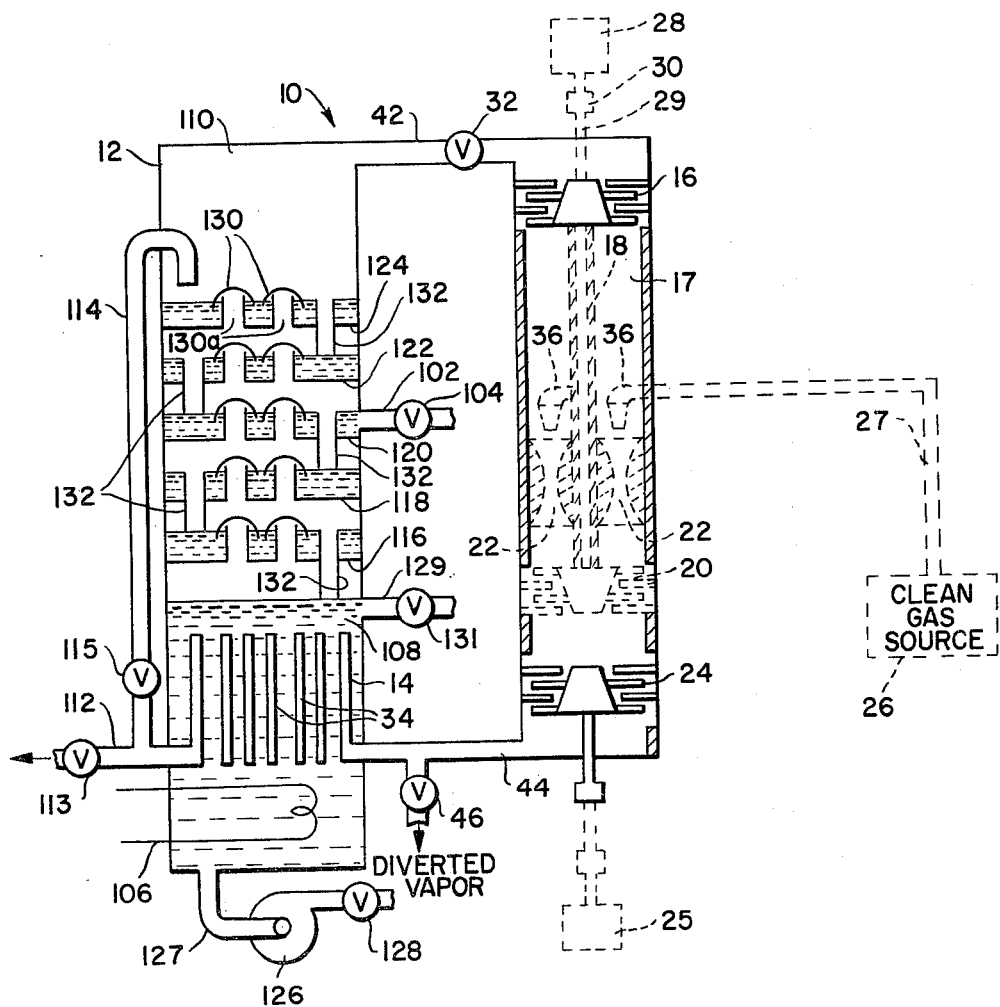
FIG. 1 illustrates schematically a single stage embodiment of the distillation system of the present invention showing an exemplary means and alternative means (in phantom) for treating the distilled low boiler vapor.

Referring now to FIG. 1, a vacuum distillation-vapor compression system is shown generally at 10. The system consists in its essential aspects of a fractional distillation boiler unit 12 including a condenser section 14 therein (although the condenser need not be housed within unit 12), a variable compression ratio turbine compressor 16, means for operating compressor 16 such as via optional turbine motor 20 and shaft 18 (shown in phantom), means for supplying additional or makeup work to the optional turbine motor 20, i.e., work not done on the turbine by the vapors passing therethrough, a vapor composition adjustment zone 17 which may contain catalysts and/or reactants and may include inlet and outlet ports (not shown) for feeding to and/or venting from the zone, all to encourage and support reaction of the vapor and conversion to more useful compositions, and a second compressor 24 downstream and independent of the turbine motor 20. The independent compressor 24 may be operated by a motive power system providing a flow of high temperature, high pressure gases to means for driving it. Instead, the compressor could be operated directly by electrical, diesel or gasoline motor mean, such as motor means 25 (shown in phantom). The means for operating compressor 16 in the absence of a turbine 20 or for supplying make-up work to the turbine may include motor means, such as motor 28, (shown in phantom) which can be powered by electricity, gasoline, diesel fuel, and the like, directly linked through shaft 29 (shown in phantom) to turbine shaft 18 for directly driving the turbine. Alternatively, or in addition, the means for supplying make-up work may include a mixing chamber 22 (shown in phantom) upstream of the turbine motor 20 and means 26 (shown in phantom) for supplying hot gases to mixing chamber 22 for direct combination with the compressed vapors from compressor 16 to motivate turbine 20. Other well known techniques for supplying energy can also be used, but are generally less desirable. It will be appreciated therefore, that the language "adding make-up work to the turbine" or similar expressions used herein are intended to contemplate any addition of work to the system, whether directly or indirectly to the turbine, where the effect of that work is to motivate the turbine.

To understand the operation of the system 10, the path of raw feed, e.g., impure water, therethrough can be charted. For purposes of this description the system of FIG. 1 is assumed to include optional turbine 20, mixing chamber 22 and a hot gas source 26 as the means for supplying make-up work to turbine 20.

The raw feed impure liquid, such as a dilute EtOH-water mixture, enters unit 12 through raw feed line 102 controlled by feed control valve 104. Electric coils 106 are employed to heat the raw feed at start-up. The raw feed line 102 may communicate directly with a raw feed source or, alternatively, with a preheating heat exchanger such as might be employed in lieu of condenser section 14 to exchange heat between the hot vapors exiting independent compressor 24 and the raw feed. The feed is directed onto center plate 120 which, notwithstanding that only five plates are illustrated, is one of many fractional distillation plates in unit 12. Each plate 116, 118, 120, 122, 124 contains a number of bubble caps 130, bubble cap pipes 130a and an overflow pipe 132. As feed enters center plate 120 it overflows through overflow pipe 132 to plate 118 below. On this lower plate, the liquid comes into contact with the vapor moving upward through bubble cap pipes 130a from the liquid reservoir 108 in the condenser section 14 of unit 12. The bubble caps 130 are so designed that the vapor passing through them must bubble through a layer of liquid on each plate before it can escape. During this bubbling process, a portion of the high boiling component in the vapor is condensed out and a portion of the low boiling component in the liquid is vaporized. Thus the vapor moving on to the next higher plates from plate 118 through bubble cap pipes 130a is richer in the low boiling constituent than the vapor which approached plate 118 from below and the liquid overflowing plate 118 to the next lower plate 116 through overflow pipes 132 is richer in the high boiling component than the liquid which reached plate 118 from plate 120. The net result of the interaction between the vapor and the liquid on each plate is that the concentration of the low boiler increases in the vapor and the concentration of the high boiler increases in the liquid. By repeating this process with a sufficient number of plates, the raw liquid feed mixture can be separated into a substantially pure low boiler vapor at 110 and a high boiler liquid reservoir at 108. The low boiler distillate is drawn off through duct 112 controlled by valve 113 and a portion of the distillate is refluxed through reflux conduit 114 and reflux valve 115 to the upper plates of unit 12 in order to maintain the supply of substantially pure low boiling component on the upper plates. The high boiling component is removed via pump 126, discharge line 127 and discharge control valve 128. A feed line 129 communicates through valve 131 with reservoir 108 to allow pure water or liquid high boiling component to be introduced therethrough. Particularly where the impure liquid feed consists of a binary mixture, such as alcohol and water, equilibrium will be reached faster if, prior to start-up, water or the high boiling component covers condenser section 14. Initially, a starter motor, such as motor 28, is energized to rotate shaft 18 through clutch and gear box 30. Compressor 16 and turbine 20, which are linked to shaft 18, also rotate when the motor 28 is operated. During start-up the variable compression ratio compressor 16 is allowed to rotate for a time sufficient for a vacuum to be drawn on the evaporative side of unit 12. The compression ratio and the extent of the vacuum is predetermined based upon the desired operating parameters of the system and the temperature of the influent impure liquid and is controlled and monitored by variable pressure valve 32 in duct 42 joining the unit 12 and first compressor 16. Means 26 for supplying hot gases to mixing chamber 22, when supplied hot gases are the means employed for supplying make-up work, are operated to motivate turbine 20 to keep it running during start-up and to heat the tubes 34 in condenser section 14.

Feed impure liquid enters system 10 through raw feed line 102 and is fractionally distilled, in the manner hereinbefore described, such that the low boiling component is vaporized at its boiling temperature, which depends on the vacuum level in the unit 12, by heat transferred from the condensing vapor in hot condenser tubes 34. Substantially pure high boiling component is removed via pump 126, discharge line 127 and discharge control valve 128. The low boiling component vapor produced at $P_1$ and $T_1$ (the pressure and temperature in unit 12) is drawn through moisture separators or entrainers (not shown) into duct 42 joining the unit 12 and the first compressor 16 and is substantially adiabatically compressed, at a ratio of from 1.2:1 to 250:1, preferably 5:1 to 100:1 and more preferably 5:1 to 50:1, by compressor 16 to $P_2$ with a resulting heating of the vapor to $T_2$. The vapor then enters reaction space 17 where, depending upon the desired end product, it may be reacted either catalytically or otherwise, it may be vented or may otherwise be treated to alter its composition. Alternatively, zone 17 may serve merely as drift space to aid in stabilizing the vapor composition. Upon exiting adjustment zone 17, the vapor, mixes with the hot, clean combustion gases emitting from injectors 36 in mixing chamber 22, which may be a mixing injector, mixing aspirator, jet mixer or any other configuration known to be suitable for mixing vapors having different pressures in such a manner that a partial vacuum is created upstream of the actual mixing point. The partial vacuum is useful in drawing the non-injected vapor into the mixing chamber and thereby for enhancing the mixing. The temperature of the combustion gas is higher than the temperature of the heated vapor at this point although there is a substantially smaller flow rate of combustion gases than of vapor. The direct mixing results in a substantially isobaric increase of vapor temperature by at least about 2° K. to $T_3$ while pressure remains substantially the same, i.e., $P_3$ equals $P_2$. The mixed vapor-combustion gas stream substantially adiabatically expands through turbine 20 to reduced pressure and temperature $P_4$ and $T_4$ and, in so doing, does work $W_2$ on the turbine to operate it. Since the turbine 20 and compressor 16 are directly linked by shaft 18, the amount of work $W_2$ done by the vapor and combustion gas on the turbine is equal to the amount of work $W_1$ done on the vapor by the compressor, i.e., $W_1$ equals $W_2$. Inasmuch as the combustion gas serves primarily to heat the vapor and since the combustion gas flow rate is only a small fraction of the vapor flow rate (e.g., about 125,000 gal/hr of vapor to less than 1,000 gal/hr of combustion gas), the work $W_2$ is largely done by the vapor in a steady state condition. The expanded and reduced temperature vapor exhausting from the turbine 20 then passes through independent compressor 24 and is substantially adiabatically compressed to increase its pressure to $P_5$ and its temperature to $T_5$. These pressure and temperature conditions, $P_5$ and $T_5$, represent the initial vapor conditions in the condenser tubes 34 as well. Therefore, the compression ratio in compressor 24 is selected to provide a final pressure at least equal to ambient and to create the desired temperature differential for effective heat transfer in the condenser tubes 34 from the condensing vapor to the feed solution entering raw feed line 102. The heat transfer temperature differential must be high enough that large volumes of feed water can be accomodated in this system within the practical limits imposed by reasonable condenser size. It is for achieving reasonable condenser size and for controlling pressure surges that the independent compressor is so important in this embodiment, particularly where, as here, the compression ratio of the independent compressor can be adjusted to accomodate variations in feed water flow rate and feed water temperature. Following condensation, purified low boiling component is drawn off through duct 112 controlled by valve 113 and a portion thereof is refluxed through reflux conduit 114 and reflux valve 115 to the upper plates of fractional distillation unit 12 in order to maintain the supply of essentially pure low boiling component on the upper plates. In an alternative operative embodiment, make-up work may be furnished by motor means, such as motor 28, the independent compressor may be directly driven by motor means, such as motor 25, and means 26 and the associated mixing and gas supply apparatus partially or totally eliminated.

Figure 1A:
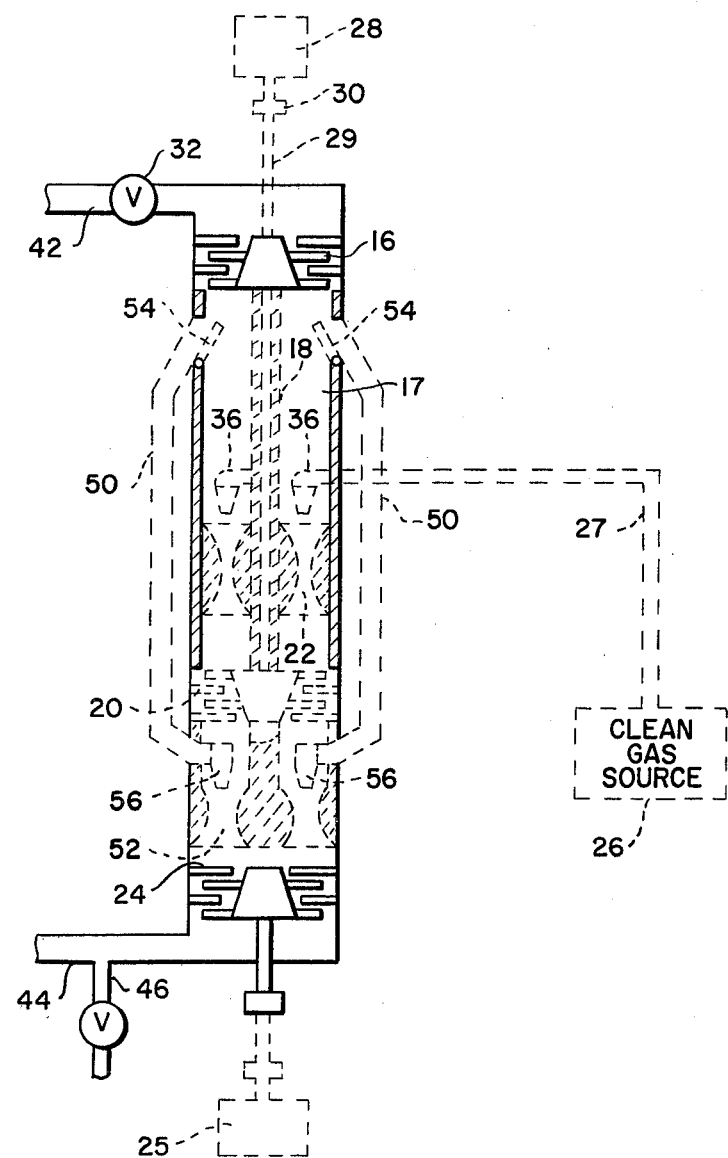
FIG. 1A illustrates schematically another single stage embodiment of the present invention showing an exemplary means and other alternative (in phantom) means for treating the distilled low boiler vapor.

FIG. 1A illustrates another embodiment of the vacuum distillation-vapor compression system shown in FIG. 1. The system of FIG. 1A differs from the FIG. 1 embodiment in the provision of optional bypass arms 50 to bypass adjustment zone 17 and, if employed, turbine 20 and a mixing chamber 52 downstream of adjustment zone 17 and turbine 20. The FIG. 1A system consists in its essential aspects of a fractional distillation boiler unit 12 including a condenser section 14 therein, a variable compression ratio turbine compressor 16, means for operating compressor 16 such as via optional turbine motor 20 and shaft 18 (shown in phantom), a vapor composition adjustment zone 17, optional turbine and adjustment zone bypass arms 50, an optional mixing chamber 52 downstream of the turbine motor 20 and adjustment zone 17, means for supplying additional or make-up work to turbine 20, i.e., work not done on the turbine by the vapors passing therethrough, and an independent second compressor 24 downstream of the optional mixing chamber 52. The work supplying means may be hot clean gas supplying means 26 for supplying hot gases, e.g. combustion gases, to mixing chamber 22 for direct combination with the compressed vapors from compressor 16 to motivate turbine 20. Alternatively, in lieu of hot clean gases, or in addition thereto, the turbine 20 (or compressor 16 if turbine 20 is not employed) can be directly driven through its shaft 18 by motor means 28, such as an electric or diesel powered motor, acting through shaft 29 and clutch and gear box 30 (shown in phantom). The independent compressor 24 may be operated by a motive power system providing a flow of high temperature, high pressure gases to means for driving it. Instead, compressor 24 could be operated directly by electrical, diesel or gasoline motor means such as motor means 25 (shown in phantom).

To understand the operation of the system of FIG. 1A the path of raw feed, e.g., impure water, therethrough can be charted. For purposes of this description, the system of FIG. 1A is assumed to include optional turbine 20, mixing chamber 22, hot gas source 26 as the means for supplying make-up work to turbine 20, bypass arms 50 and mixing chamber 52. Initially, a starter motor, such as motor 28 is energized to rotate shafts 28 and 29 through clutch and gear box 30. Compressor 16 and turbine 20, which are linked to shaft 18, also rotate when the motor 28 is operated. During start-up, the compressor 16 is allowed to rotate for a time sufficient for a vacuum to be drawn on the evaporative side of boiler 12. The extent of the vacuum is predetermined, as will be seen hereinafter, based upon the desired operating parameters of the system and the temperature of the influent impure liquid and is controlled and monitored by variable pressure valve 32 in duct 42 joining the unit 12 and compressor 16. Optional means 26 for supplying hot gases to mixing chamber 22, if present, may be operated to motivate turbine 20 to keep it running during start-up and to heat the tubes 34 in the condenser section.

Referring to FIG. 1A, it can be seen that the vaporized low boiling component of the impure liquid at $P_1$, $T_1$ is drawn into duct 42 leading to turbine compressor 16. The pressure $P_1$ is maintained in unit 12 at the desired level by pressure regulating valve 32 disposed in duct 42. The vapor is substantially adiabatically compressed at a ratio of from 1.2:1 to 250:1, preferably 5:1 to 100:1 and more preferably 5:1 to 50:1, in compressor 16 to $P_2$, $T_2$ and, upon leaving compressor 16, can proceed either through adjustment zone 17, mixing chamber 22 and turbine motor 20 or can be diverted by by-pass control valves 54 into by-pass arms 50. Although two by-pass arms 50 are shown for descriptive convenience, there may, in fact, be only one by-pass arm or there may be multiple by-pass arms. Moreover, the vapor which flows into the by-pass arms may be at the same, higher or lower pressure than the vapor which proceeds through turbine motor 20. Inasmuch as turbine compressors are frequently multi-stage units, and since the extent of compression depends on the number of stages through which the vapor passes, it is a simple matter to direct the flow into the by-pass arms 50 from a different compression stage than the flow which proceeds through turbine 20.

In accordance with this embodiment, it is contemplated that as little as a fraction of 1% or as much as 100% of the vapor flow exiting compressor 16, e.g., 0.001–100% by volume, preferably 0.15–95%, may be diverted into by-pass arms 50. Although it is unlikely that in practical operation the amount of vapor by-passing zone 17 and turbine 20 will be at either extreme, the system of FIG. 1A is operative at the extremes as well as at any point therebetween. The selection of the amount of flow to be diverted depends upon the economics sought from the process, the volume flow rate required and whether reduced operating expenditures take precedence over capital equipment expenditures, or viceversa.

Assuming that direct mixing with hot gases is the method chosen to add work to the system upstream of or at turbine 20, the vapor which proceeds through compressor 16 is passed through adjustment zone 17 where it either reacts or is otherwise altered to form a more desirable composition vapor or the vapor composition stabilizes by utilizing zone 17 as drift space. The resulting vapor is substantially isobarically admixed in mixing chamber 22 with hot, clean gases supplied from source 26 through duct 27 and emitted from injectors 36. The mixing chamber 22 may be a mixing injector, mixing aspirator, jet mixer or any other configuration known to be suitable for mixing vapors having different pressures in such a manner that a partial vacuum is created upstream of the actual mixing point. The partial vacuum is useful for drawing the non-injected vapor into the mixing chamber and thereby enhancing the mixing. The mixture of vapor and gases operate turbine motor 20 which is linked by shaft 18 to compressor 16. The temperature of the added gas is sufficiently greater than the temperature of the vapor to heat the vapor, at substantially constant pressure (i.e., $P_3 = P_2$), by at least about 2° K. to $T_3$ before the heated vapor does work $W_2$ on the turbine 20. Because of the direct shaft link between turbine 20 and compressor 16, the work $W_2$ done on the turbine equals the work $W_1$ done by the compressor on the vapor in substantially adiabatically compressing it. The vapor substantially adiabatically expands through turbine 20 with a resultant pressure and temperature drop to $P_4$, $T_4$.

The vapor which is diverted through by-pass arms 50 is at a temperature and pressure which equals $T_2$, $P_2$ in the case where all vapor is equally compressed in compressor 16. The by-pass vapor is recombined with the vapor passing through zone 17 and turbine 20 in mixing section 52 wherein the by-pass vapor is injected through injectors 56 into the stream of vapor exhausting the turbine. Mixing section 52 can have any suitable configuration for efficient mixing of vapors. The effect of this vapor mixing is to compress and heat the vapor exiting turbine 20 to $P_5$, $T_5$, whereupon the mixed vapor proceeds to independent compressor 24. The $P_5$, $T_5$ vapor from mixing section 52 is further compressed in a substantially adiabatic fashion to increase its pressure and temperature to $P_6$, $T_6$ and then passed through return duct 44 to condenser tubes 34 in unit 12. As with the FIG. 1 embodiment, the compression ratio in independent compressor 24 is selected to provide a final pressure at least equal to ambient and to create a high enough heat transfer temperature differential between the returning vapor at $T_6$ and the feed water at $T_1$ that large volumes of feed water can be accomodated in this system within the practical limits imposed by reasonable condenser size. The vapor condenses in tubes 34 giving up its heat of vaporization to the feed liquid entering the system. Purified low boiling component may be drawn off and then refluxed through duct 112 and reflux conduit 114. Vaporized low boiling component may be diverted through line 46 if desired.

It will be appreciated that bypassing adjustment zone 17 and/or the turbine 20 with at least a portion of the vapor together with the mixing action created by injectors 36 upstream of the turbine and injectors 56 downstream of the turbine have the net effect of creating a vacuum at the turbine outlet which materially eases the task of maintaining turbine rotation at a level sufficient that compressor 16 is able to perform a quantity of work $W_1$ in compressing the vapor. Nevertheless, a quantity of work $W_2 = W_1$ must still be done on turbine 20 by the vapor passing therethrough. Since the quantity of vapor passing through the turbine is decreased to the extent of the bypass, not as much vapor is available to run the turbine and the energy content of the bypass vapor must be compensated for, as, for example, by the addition of thermal energy via the gases, which may be combustion gases, injected into mixing chamber 22 through injectors 36. The hot gases as well as the additional thermal energy may be furnished in any form, as long as the gases are clean, from any available source. Suitable sources may include hot combustion gas sources, high temperature, high pressure steam sources, and the like. It will be appreciated, however, as previously indicated, that hot gas mixing to raise the thermal energy of the vapor and thereby permit the vapor to do the quantity of work $W_2$ on the turbine is not the only means of adding make-up work. Instead, the hot gas source 26, duct 27, injectors 36 and mixing chamber 22 can all be eliminated and the quantity of make-up work needed to reach $W_2$ which is not supplied by the vapor can be furnished by directly driving the turbine through mechanical means, such as motor 28. Where, however, hot gases are added to the vapor to raise its thermal energy, it is preferred that direct mixing of gases and vapor occur. Alternative vapor heating configurations, such as by indirect heat exchange through a conventional heat exchanger as taught in U.S. Pat. No. 3,423,293—Holden, is wasteful of thermal energy due to transfer inefficiencies and the resulting need for higher temperature heat transfer mediums, and is therefore uneconomical. Improved vapor and combustion gas mixing and more uniform temperature distribution along mixing chamber 22 can be achieved by use of multiple nozzle injectors (not shown) in chamber 22.

Figure 1B:
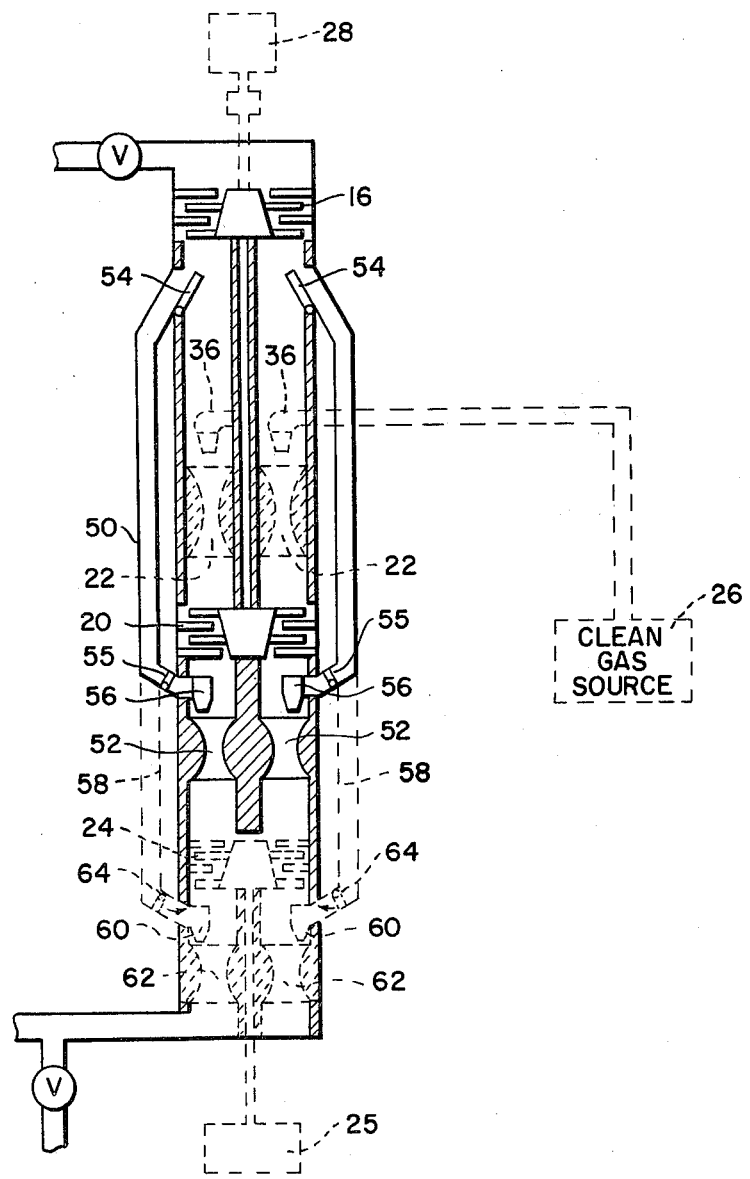
FIG. 1B illustrates schematically another single stage embodiment of the present invention showing a different exemplary means and still another alternative (in phantom) means for treating the distilled low boiler vapor.
Figure 1B:
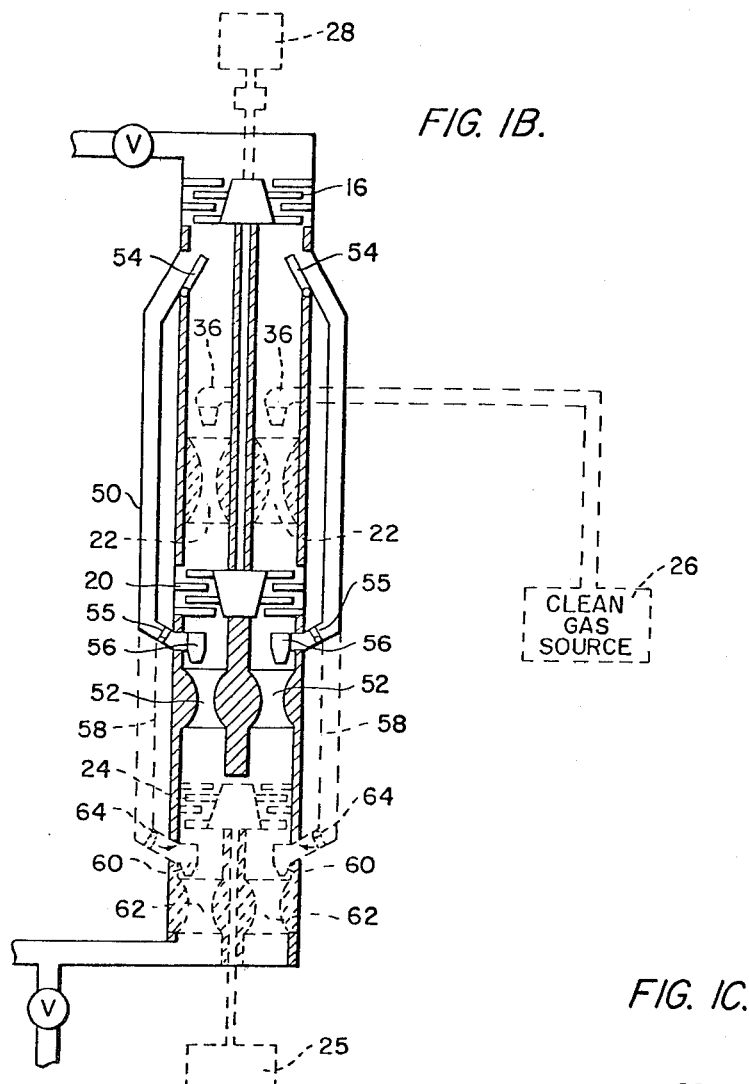

FIG. 1B illustrates still another embodiment of the present invention wherein the system of FIG. 1A is modified by making independent compressor 24 optional and by adding an optional third mixing section 62, similar to mixing sections 22 and 52, wherein vapor flowing in bypass arms 50 may be injected downstream of optional independent compressor 24 through optional bypass arms 58 and injectors 60. Such an arrangement provides a large degree of operational flexibility and permits continuous operation even under adverse conditions. Whether vapor flowing in bypass arms 50 is admixed with vapor expanding through turbine 20 in mixing chamber 52 through injectors 56 or with higher pressure and temperature vapor downstream of independent compressor 24 in mixing chamber 62 through injectors 60 is controlled by bypass flow control valves 55 and 64, respectively. As in the embodiments of FIGS. 1 and 1A, the additional energy needed to drive turbine 20 may be furnished from clean gas source 26 as thermal energy, from motor means 28 as mechanical energy, or from any other sutiable source. In a similar manner, optional independent compressor 24 may be directly driven through motor means 25 or may be driven in any other suitable way.

The systems illustrated in FIGS. 1, 1A, 1B, and the other embodiments to be described hereinafter are useful even when the impure liquid feed contains dissolved salts which can precipitate and form scale on the outside of the condenser tubes and on the boiler walls at relatively high evaporation temperatures. Because scale deposits interfere with efficient heat transfer between the condensing vapor in the tubes and the feed liquid in the evaporator, it is undesirable to operate the system at an evaporator temperature at which scaling occurs. Therefore, when sea water containing calcium sufate, magnesium hydroxide, calcium carbonate, and the like, is the liquid feed, since these salts are more soluble in cold sea water than in sea water above about 160° F., at temperatures above 160° F. scale will rapidly form on the hot tubes and condenser surfaces and will, in a short time, render the system operative only at very low thermal efficiencies. Therefore, if sea water is the liquid feed, evaporator temperature ($T_1$) should be kept below 160° F. and preferably below 150° F. The system can still treat very large volumes of liquid feed in an efficient manner by maintaining a vacuum in the boiler at a level such that the boiling of the liquid feed is accomplished within the noscaling temperature limitations.

The lower limit of $T_1$ is dictated by practical considerations since the system is unsuited for treating solid feed. Therefore, for basically water feeds, $T_1$ should not be below the freezing point of water at ambient conditions, which at 1 atm. is 0° C. (32° F.) corresponding to a $P_1$ under substantially saturated conditions of 0.006 atm. $T_1$ is suitably at 33° F. or above. For basically water feeds where water is the low boiling feed component, $T_1$ is preferably almost as high as the boiling point of water at 1 atm., which is 212° F., e.g., at about 211° F. and 0.99 atm. For non-aqueous systems or aqueous binary, ternary, etc systems, where the low boiling component is other than water, it may be desirable to practice the invention at any temperature less than about the critical temperature, i.e., the temperature above which the vapor cannot be condensed regardless of the pressure applied thereto, although it should be appreciated that the temperature may exceed the critical temperature for any component of the vapor. Each system must be operated at evaporator temperatures and pressures, compression ratios, and the like, to meet the particular fractionation requirements of the impure liquid feed and the flow rate and cost requirements of each user. Therefore, depending upon whether a user desires to reduce operating costs at the expense of capital costs, or vice versa, one or more systems can be operated together to yield the desired flow rate and cost. The examples and data provided hereinafter are useful in making a choice of system parameter starting points necessary to meet a potential users needs.

EXAMPLE I

The system of FIG. 1 employing the optional turbine motor 20 and furnishing make-up work to the turbine via motor means 28 was utilized to fractionally distill a 6–12% by weight EtOH containing EtOH/H$_2$O mixture. It is known that the EtOH/H$_2$O azeotrope disappears below about 100 mm Hg total pressure. Accordingly, it is an object of the Example to operate evaporator 12 below 100 mm Hg. For purposes of illustration the fractional distillation system is adjusted to operate at a $P_1$ of 78.6 mm Hg (1.5199 psia). At this pressure pure ethyl alcohol boils at 30° C.(86° F.) and pure water boils at 47.78° C. (116.2° F.). To speed the rate at which equilibrium is reached, sufficient pure water is initally introduced via line 129 and valve 131 to cover evaporator coils 34.

A 6–12% by weight EtOH and water mixture is introduced through raw feed line 102 and associated valve 104 onto plate 120. Heating coil 106 heats the water to 116.2° F. at which temperature and at a pressure of $P_1 = 78.6$ mm Hg the water boils. As the pure water vapor rises through the bubble cap pipes it heats the raw feed solution on the plates and condenses, returning to the bottom of evaporator 12 through overflow pipes 132. The mixture on the plates, depending upon composition, evaporates at some temperature between 86° F. and 116.2° F., with the low boiling EtOH component rising with the vapor until the tops are reached at 110 where there is substantially pure EtOH at a temperature of 86° F. and a pressure of 78.6 mm Hg. This EtOH vapor proceeds through duct 42 and is compressed in first compressor 16, allowed to drift through adjustment zone 17, expanded passing through turbine 20 and recompressed by second independent compressor 24 to a final pressure, $P_5$, above ambient pressure. For illustrative purposes $P_5$ is about 1000 mm Hg (19.337 psia). At this pressure the EtOH component condenses at a $T_5$ of about 85° C. (185.8° F.).

To demonstrate that the instant can in fact purify large volumes of the binary EtOH/water mixture using equipment, specifically a condenser, of reasonable size and availability, it is assumed herein that compressor 16 can maintain the boiler pressure $P_1$ at 78.6 mm Hg. In this case, the rate of flow of EtOH vapor is solely dependent on the rate that the heat of vaporization is transferred to the feed liquid. The heat of vaporization or of condensation, $H_c$, of EtOH is found in the literature as 352.6 BTU/lb. See, e.g., J. Timmermans, "Physico-Chemical Constants of Pure Organic Compounds" (1950). The temperature difference between the condensing EtOH vapor and the feed liquid at $P_5 = 1000$ mm Hg is $\Delta T_{LM}$. $\Delta T_{LM}$ is the log mean temperature difference during condensation which, together with the initial temperature of the impure liquid, $T_1$, and the desired final distillate effluent temperature, $T_D$, determines the required condenser size.

$$\Delta T_{LM} = \Delta T_{max} - \Delta T_{min}/\ln(\Delta T_{max}/\Delta T_{min})$$

where $\Delta T_{max} = T_5 - T_1, \Delta T_{min} = T_D - T_1$, and $T_D$ is the distillate temperature selected to be equal to or less than the vapor condensation temperature and greater than $T_1$. In this case, $T_D = 125°$ F. (51.7° C.); $\Delta T_{max} = 185.8 - 116.2 = 69.6°$ F.; $\Delta T_{min} = 125 - 116.2 = 8.8°$ F.; and $\Delta T_{LM} = 29.4°$ F.

The surface area A in square feet of a condenser required to condense R gallons/hr of condensate at 185.8° F. having a heat of vaporization or condensation, $H_c$, of 352.6 BTU/lb through a temperature differential of 29.4° F. in a stainless steel condenser having a coefficient of heat transfer U, conservatively taken to be 1500 BTU/hr—°F.—ft$^2$ can be determined from the following relationship:

$$A = RH_c/U\Delta T_{LM}$$

Rewriting in terms of R:

$$R = AU\Delta T_{LM}/H_c$$

It is known that a conventional condenser unit, such as is manufactured by the Pfaudler Company of Rochester, N.Y., which is 5 feet long and 5 feet wide has an effective surface area for heat transfer of 2988 ft.$^2$. Therefore, the length L of such a unit necessary to provide A ft.$^2$ of surface area is denoted by the formula:

$$A/2988 \times 5 = L$$

$$A = 2988L/5$$

Inserting the aforementioned values for U, $H_c, \Delta T_{LM}$, and A, assuming L=10′ and converting the result to gallons/hour yields:

R = 117,508 gallons/hr.

EXAMPLE II

The cost to produce the flow R determined in Example I can be approximated from available data since, in a system without bypass, the BTU cost is only dependent on the initial and final vapor states. Of course such a calculation necessarily neglects inefficiencies due to frictional, heat and other losses.

Cost (BTU/lb) = $C_p(T_5 - T_1)$

It is known that $T_1 = 30°$ C. = 303° K. It is also known that $P_1 = 78.6$ mm Hg and $P_5 = 1000$ mm Hg. $T_5$ can be calculated from the ideal gas law applied to adiabatic compressions and expansions and assuming that the heat capacities at constant volume and pressure, $C_v$ and $C_p$, are constant, it is known that:

$$T_5/T_1 = (P_5/P_1)^b$$

where $b = \gamma - 1/\gamma$ and $\gamma = C_p/C_v$.

Standard tables show that at 1 atm, $\gamma = 1.13$ for EtOH gas at least over the range 0° to 90° C. Therefore, as long as the pressure is maintained at less than about 2 atmospheres, use of $\gamma = 1.13$ will not introduce an unacceptable error. Substituting into the foregoing equation for $T_5/T_1$ and solving for $T_5$ yields:

$T_5 = 553.1°$ K. = 280.1° C.

Interpolating in standard tables showing $C_p$ for EtOH over the range 0° C.–500° C., it can be determined that use of $C_p = 0.5$ BTU/lb—°F. is a conservative approximation for cost calculations. The cost in BTU/lb with $C_p = 0.5, T_5 = 280.1°$ C. and $T_1 = 30°$ C. and converting °C. to °F. becomes:

Cost = 225 BTU/lb

Converting units into gallons and assuming that the cost to produce energy is about $5.00/1,000,000 BTU, we find:

Cost = $7.15/1000 gallons.

EXAMPLE III

Using the methods described in U.S. Pat. No. 4,035,243 and in the aforementioned copending applications, and assuming that the raw feed is impure water and the object is to purify large volumes of the water at minimum energy, capital and operating costs, Table I shows the resulting aproximate cost and flow values for a representative sampling of $T_1$ values and compression ratios (CR). For each analysis, the column denoted "Configuration" indicates the numeral designations of the major components comprising the vapor treatment section as illustrated in FIG. 1A.

| T₁ (°F.) | P₁ (psia) | CR | P₂ (psia) | T₂ (°F.) | P_f* (psia) | T_f** (°F.) | $/1000 gal Cost*** | gal/hr Flow' | Configuration |
|---|---|---|---|---|---|---|---|---|---|
| 70 | 0.3629 | 25 | 9.072 | 682 | 15 | 212 | 14.03 | 56,131 | 16,17,20,24 |
| 122 | 1.7891 | 25 | 44.73 | 780 | 15 | 212 | 7.32 | 59,523 | 16,17,20,24 |
| 122 | 1.7891 | 25 | 44.73 | 780 | 44.73 | 274 | 13.12 | 56,269 | 16,17,24 |
| 70 | 0.3629 | 85 | 30.84 | 1040 | 30.84 | 252 | 18.52 | 54,026 | 16,17,24 |
| 150 | 3.7184 | 25 | 92.96 | 821 | 15 | 212 | 4.43 | 59,931 | 16,17,20,24 |
| 200 | 11.526 | 15 | 172.89 | 784 | 15 | 212 | 0.88 | 29,090 | 16,17,20,24 |
| 300 | 67.005 | 25 | 1675.0 | 1126 | 70.86 | 303.8 | 0.16 | 9,942 | 16,17,20,24 |
| 85 | 0.5958 | 50 | 29.79 | 910 | 25.15 | 147** | 1.16 | 99,689 | 16,17,20,50, 52,24 (bypass chosen to be 7.5%) |

Figure 1C:
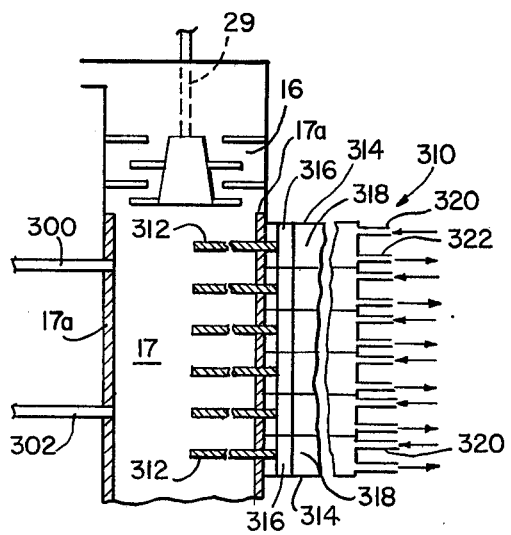
FIG. 1C illustrates schematically various exemplary means for introducing reactants and/or catalysts into the vapor composition adjustment zone of the various embodiments of the present invention.

*P_f = final pressure at which condensation starts (P₅ or P₆ depending upon configuration)
**T_f = final temperature at which condensation starts (T₅ or T₆ depending upon configuration)
*** = Cost assumes energy cost at $5.00/1,000,000 BTU
' = Flow assumes a condenser length of ten feet FIG. 1C illustrates exemplary means for introducing reactants and/or catalysts into the path of vapor exiting compressor 16 in vapor composition adjustment zone 17. These exemplary means are equally applicable to all embodiments of the present invention. Thus, reactants or catalysts may be pumped, sprayed or otherwise injected into space 17 via conduits 300,302 which communicate with space 17 through wall 17a enclosing said space. Although two conduits are illustrated, it will be appreciated that any number of conduits can, in fact, be provided depending upon the needs of the reaction occurring in space 17. Alternatively, or in addition to reactant and/or catalyst conduits 300,302, a hydraulic system 310 may be affixed to enclosing wall 17a or otherwise associated with vapor composition adjustment space 17 in a manner which allows the removable insertion of catalyst means 312 through wall 17a into the path of vapor exiting compressor 16. System 310 comprises a plurality of hydraulic cylinders 314, each including a reciprocating piston 316 having a catalyst means 312 affixed thereto for slidable movement into and out of space 17 through wall 17a. Hydraulic fluid is pumped into or forced from fluid space 318 within cylinder 314 through hydraulic fluid inlet line 320 and removal line 322. When hydraulic fluid is pumped via inlet line 320 into fluid space 318, piston 316 is forced to slide within cylinder 314 toward wall 17a. In so moving, piston 316 insets the catalyst means 312 into space 17. In like manner, when piston 310 slides in cylinder 314 away from wall 17a, the catalyst means 312 is removed from space 17. At the same time, of course, hydraulic fluid is removed from fluid space 318 via removal line 322. Catalyst means 312 may include, for example, catalysts such as pure metals, metallic oxides, salts or mixtures of several substances in the form of an activated metal gauze or screen. One particularly useful catalyst is platinized asbestos. When system 310 comprises a plurality of cylinders for removably inserting a plurality of catalyst means 312 into space 17, the catalyst means may all be the same catalyst or each may comprise a different catalyst or some may be the same and some different depending upon the requirements of the reaction occurring in space 17. It will, of course, be appreciated that the pistons need not be hydraulically operated but can be mechanically or otherwise driven, such as by motor means.

One exemplary use for reaction space 17, particularly where the raw feed liquid contains a useful amount of crude oil, is for catalytic cracking to convert straight-run high boiling point distillate fractions to simpler substances with lower boiling points. Typically, the gases obtained as byproducts of the cracking process are rich in olefinic hydro-carbons such as ethylene, propylene and butylene. Inasmuch as cracking reactions require a finite period of time with the gases at high temperature and pressure in contact with the catalysts, space 17, located downstream of compressor 16 and adapted to contain a plurality of catalyst means 312, is ideally suited for this type reaction.

Exemplary of catalytic cracking reactions which may occur in space 17 are the following:

$C_{14}H_{30} \rightarrow C_{12}H_{26} + C_2H_4$
$C_{12}H_{26} \rightarrow C_6H_{14} + C_5H_{12} + C$
$C_{12}H_{26} \rightarrow C_7H_{16} + C_5H_{10}$
$C_{14}H_{30} \rightarrow C_{11}H_{24} + C_3H_6$ Another exemplary application of space 17 is for catalytic polymerization, particularly where the catalytic polymerization occurs downstream of the catalytic cracking. This can be accomplished by forming the downstream catalyst means 312 of phosphoric acid impregnated diatomaceous earth and, thereby, causing the upstream produced olefin gases to react and polymerize into longer chain length molecules. In this manner, there can be an increased production of gasoline as a result of sequential cracking and polymerization along the same path length. If desired, a portion of the fuel produced could be used to provide power to the distillation system. A typical high pressure gas phase polymerization reaction using a sulfuric or phosphoric acid catalyst supported by a solid impregnated with the catalyst is the following:

isobutane + propylene → 2,2,3 trimethylbutane

The trimethylbutane produced by this reaction has an octane number of 125.

It is comtemplated that a catalytic cracking-polymerization system such as hereinbefore described can be installed within a ship for the purpose of reclaiming spills of such petrochemical materials as crude oil, gasoline, heating oil, petrochemical solvents, and the like. The capability of the present system to produce its own fuel by catalytic cracking and polymerization in space 17 obviates the need for the ship to carry large amounts of fuel to power the reclamation apparatus. As a result, petrochemical reclamation from spills can be rapidly, efficiently and economically accomplished.

Figure 2:
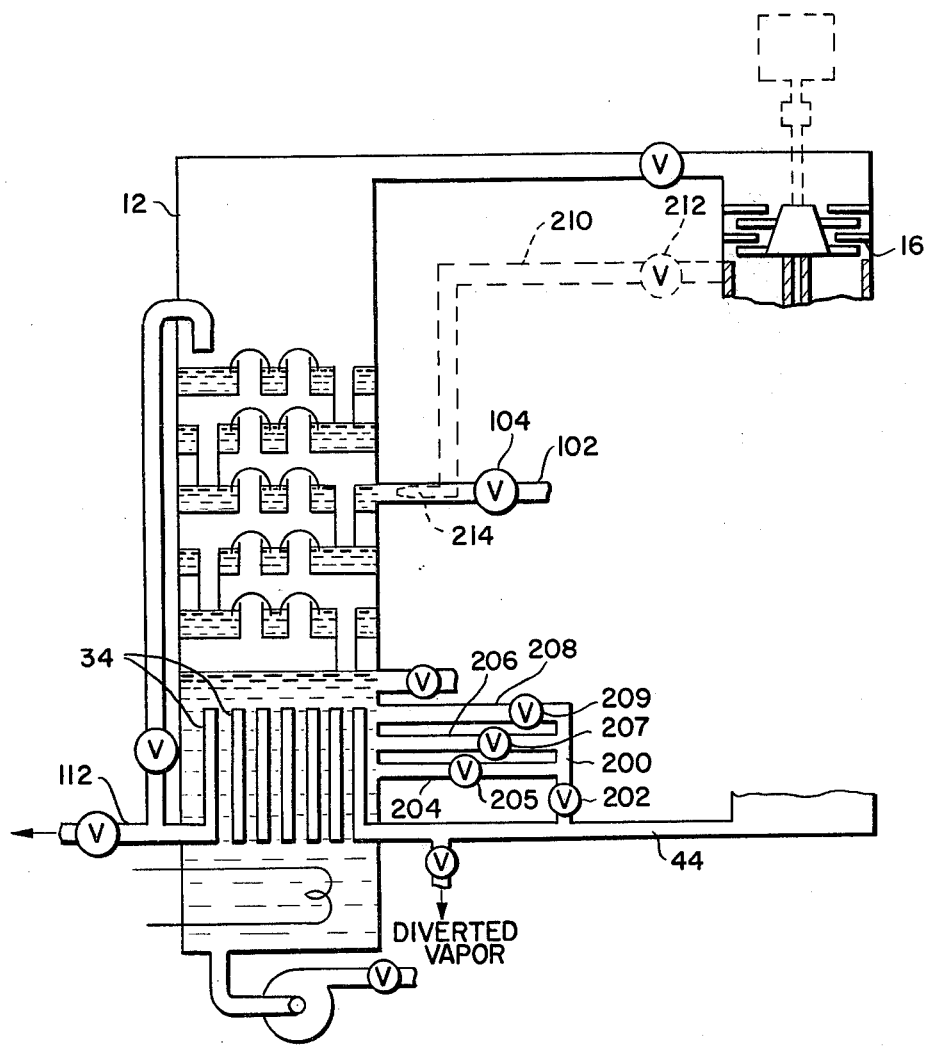
FIG. 2 illustrates schematically the single stage embodiment of FIG. 1, with the vapor treatment section deleted, including means for diverting a portion of the effluent vapor for direct mixing with the raw feed liquid.

FIG. 2 illustrates a modification which is equally applicable to all embodiments of the present invention; indeed to all vacuum and flash distillation systems. In accordance with this modification, a fraction of the compressed vapor returning to the condenser tubes 34 through duct 44 is diverted and directly injected into the fractional distillation evaporator 12 where it mixes with the impure feed liquid therein, giving up its latent heat of vaporization and raising the temperature of the feed liquid in the evaporator to $T_1$. This is particularly useful and important where the raw feed entering duct 102 is primarily water and/or the low boiling component is primarily water and the raw feed is relatively cold, e.g., water at about 33–70° F. If the temperature in evaporator 12 is maintained at such a low temperature, it is necessary for $P_1$ to also be low for boiling to occur at $T_1$. However, it is very expensive to draw and maintain a high vacuum in the boiler and, rather than do so, it may be desirable to raise the raw feed temperature to a value at which the system may be more economically operated. The expense of raising the raw feed temperature to $T_1$ by diverting a fraction of the returning vapor and direct mixing it with the feed liquid is readily measured since whatever flow is diverted does not exit the system as condensed low boiling component through line 112. On the other hand, direct mixing in the boiler is a far more efficient means of heating the raw feed than, for example, by diverting the returning vapor through an external heat exchanger in which it can heat raw feed or by passing all the returning vapor through condenser tubes 34, as in the other embodiments of this invention.

In FIG. 2, the details of the vapor treatment section of the system are not shown since this modification is equally applicable to all embodiments described herein. Hot vapor directed to the condenser tubes 34 through return duct 44 is at a temperature, $T_f$, and has an enthalpy, $h_f$. A portion of this vapor is diverted through duct 200 and its associated valve 202 into and through ducts 204, 206 and 208 and their respective valves 205, 207 and 209 for injection back into evaporator 12. Although three injection ducts are shown, it will be appreciated that any number of such ducts may, in practice, be used. The remaining or undiverted vapor continues through duct 44 into condenser tubes 34 and exits the system as purified condensed low boiling component through line 112. The fraction of the vapor which must be diverted to heat the raw feed can be calculated by assuming that the temperature of the impure raw feed liquid in feed duct 102 is $T_o$ and its enthalpy is $h_o$. The enthalpy change required, per pound of raw feed, to heat from $T_o$ to $T_1$ is ($h_f-h_o$). In order to produce this change, a fraction, $F_D$, of returning vapor, e.g., steam or other low boiling component, at $h_f$ must be diverted through duct 200 and admixed with the feed liquid, condensing in the process and having a final temperature of $T_1$. For one pound of returning vapor, the enthalpy change is $h_f-h_l$ and the fractional change is $F_D$ ($h_f-h_l$). Since the enthalpy change in the condensing vapor must equal the enthalpy change of the raw feed, it can be determined that:

$$F_D = h_l - h_o / h_f - h_o$$

From this relationship the fraction of compressed vapor diverted form duct 44 into duct 200 can be determined for various raw feed temperatures and desired boiler temperatures. By similar well known techniques the flow rate of low boiling effluent, $R_D$, which continues on through the condenser tubes and exits line 112 can be readily calculated.

An optional aspect of the system shown in FIG. 2 involves the use of return line 210 and associated valve 212 (shown in phantom) to divert a small portion of the flow exiting compressor 16 back to raw feed duct 102 wherein it is injected through injector 214 (shown in phantom). In this way, the vapor injected through injector 214 will create a pumping effect in duct 102 to aid the feed of liquid therethrough while, at the same time, heating the incoming feed liquid. Line 210 is optional, although useful, because its contribution to the heating of the raw feed is small compared to the vapors injected directly into evaporator 12 through ducts 204, 206 and 208 and because the vacuum drawn by compressor 16 is generally adequate to draw the raw feed into the boiler.

The invention has thus far been described in its simplest forms and has, in each embodiment, included but a single turbine compressor operated, where utilized, by a single turbine motor. However, the configuration of the turbine compressor 16/turbine motor 20 need not be as simplistic as shown in FIG. 1, 1A or 1B. Rather, considerable flexibility can be introduced into the system if the compressor, the turbine, the compressor-turbine combination or the compressor-mixing chamber-turbine combination is configured to meet the requirements and demands of the particular system. For illustrations of particular arrangements which are useful and are generally operable in the systems shown in FIGS. 1, 1A and 1B, attention is invited to FIGS. 3–10 and the description thereof which follows in which the numerical designations of FIGS. 1, 1A and 1B have been used for convenience and in which it has been assumed that make-up work is supplied, at least in part, by direct mixing of hot gases. It will, of course, be appreciated that FIGS. 3–10 are equally applicable in conjunction with the other embodiments and/or where no hot-gas make-up work is utilized.

Figure 3:
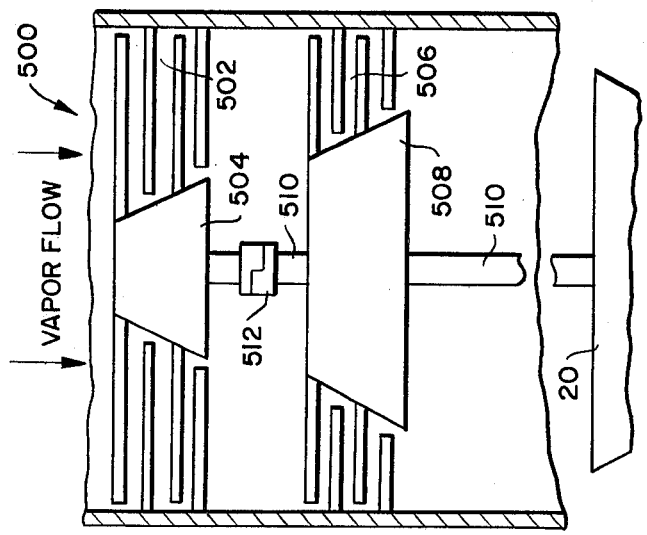
FIG. 3 illustrates schematically a clutched compressor unit which can be operated by a turbine motor as an optional turbine-compressor unit useful in the many embodiments of the present invention.

Referring first to FIG. 3, there is illustrated schematically a clutched compressor unit designated by the numeral 500, which unit may be used in lieu of turbine compressor 16. The clutched compressor unit 500 may be operated by a turbine 20 (partially shown) and includes a first compressor 502 having a compressor spindle 504 and a second compressor 506 having a compressor spindle 508 which is substantially larger than is spindle 504. Spindles 504 and 508 are linked through shaft 510 and clutch and gear box 512. Clutch and gear box 512 can cause the smaller spindle to rotate at a different velocity than the larger spindle, i.e., clutch and gear box 512 may be a variable gear box generally similar to an automobile transmission, which permits the compression ratio to be varied at will. Such a system is valuable as an aid in adjusting system operating variable depending upon the density of the vapor and the need to increase or decrease the flow rate through the system.

Figure 4:
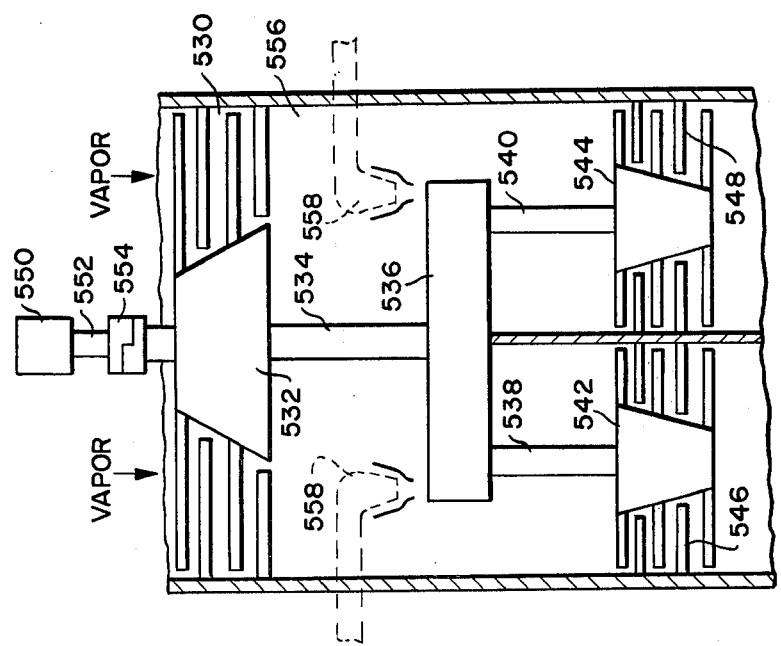
FIG. 4 illustrates schematically two turbine motors operating a single turbine compressor as an optional turbine-compressor unit useful in the many embodiments of the present invention.

FIG. 4 illustrates two turbine motors operating a single turbine compressor through a clutch and gear box. Compressor 530 has its spindle 532 linked through shaft 534 to clutch and gear box or transmission gear box 536. Shafts 538 and 540 link gear box 536 with turbine spindles 542 and 544 of turbines 546 and 548. In operation, starting motor 550 acting through shaft extension 552 and clutch 554 starts spindle 532 of compressor 530 rotating. Power is transmitted through shaft 534 to gear box 536 and, through shafts 538 and 540, spindles 542 and 544 of turbines 546 and 548 are also caused to rotate. But, clean combustion gases are mixed with the vapor flowing through space 556 as the gases are emitted into space 556 through injectors 558. The combined vapor flow and combustion gases transmit rotary power to turbines 546 and 548 and through transmission gear box 536 to compressor 530. A particular advantage of this configuration is that it is more flexible than two separate compressor-turbine combinations and, at the same time, more economical.

Figure 5:
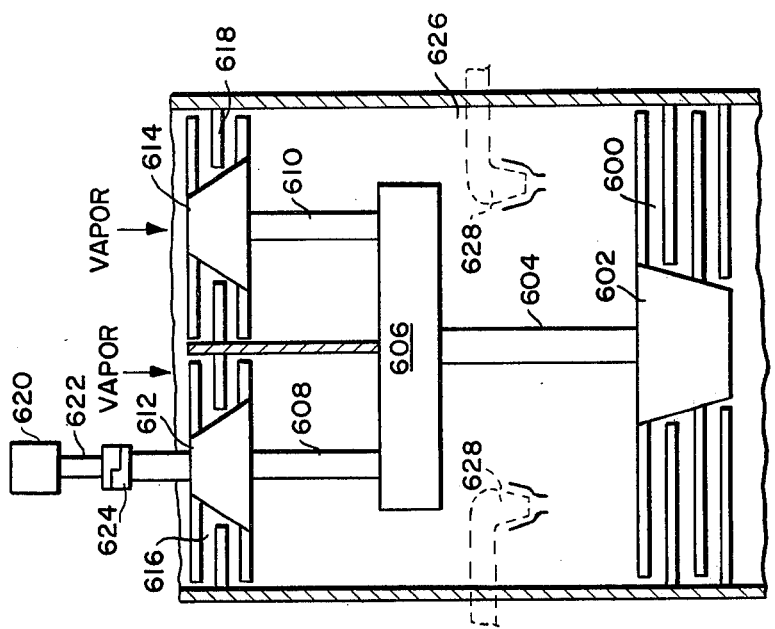
FIG. 5 illustrates schematically a single turbine motor operating two turbine compressors as an optional turbine-compressor unit useful in the many embodiments of the present invention.

FIG. 5 illustrates a single turbine motor having a spindle 602 linked through shaft 604 to gear box 606 which gear box is directly linked through shafts 608 and 610 to the spindles 612 and 614 of compressors 616 and 618. In operation, starting motor 620 operating through shaft extension 622 and clutch 624 starts spindle 612 of compressor 616 turning and, in turn, causes compressor 614 and turbine 600 to also rotate. Hot, clean combustion gases are mixed with the vapor flowing through space 626 as the gases emit from injectors 628. The combined vapor flow and hot combustion gas flow motivates turbine 600 which, through gear box 606, can operate either or both of the compressors 616 and 618. This configuration has advantages similar to those of the configuration illustrated in FIG. 4.

Figure 7:
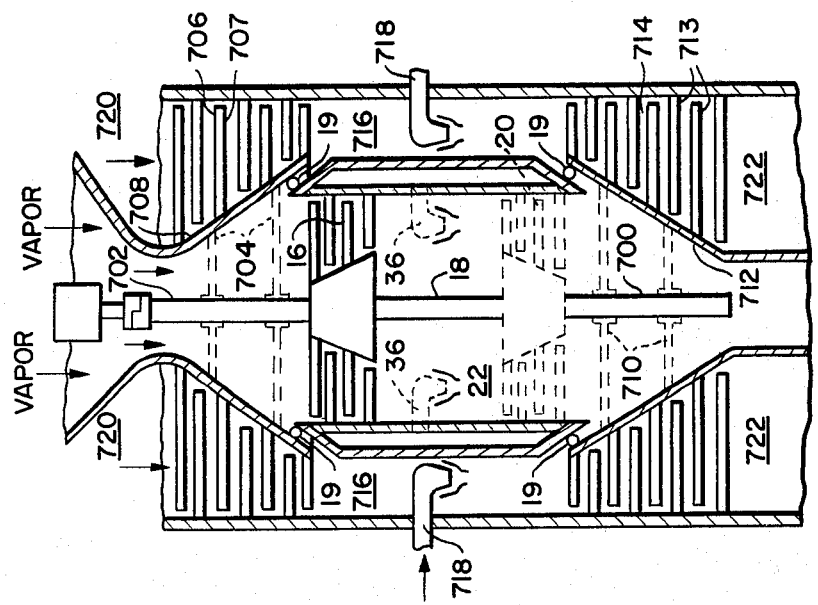
FIG. 7 illustrates schematically concentric compressor-turbine combinations, one of which combinations can be powered by dirty, hot gases, as an optional turbine-compressor unit useful in the many embodiments of the present invention.
Figure 6:
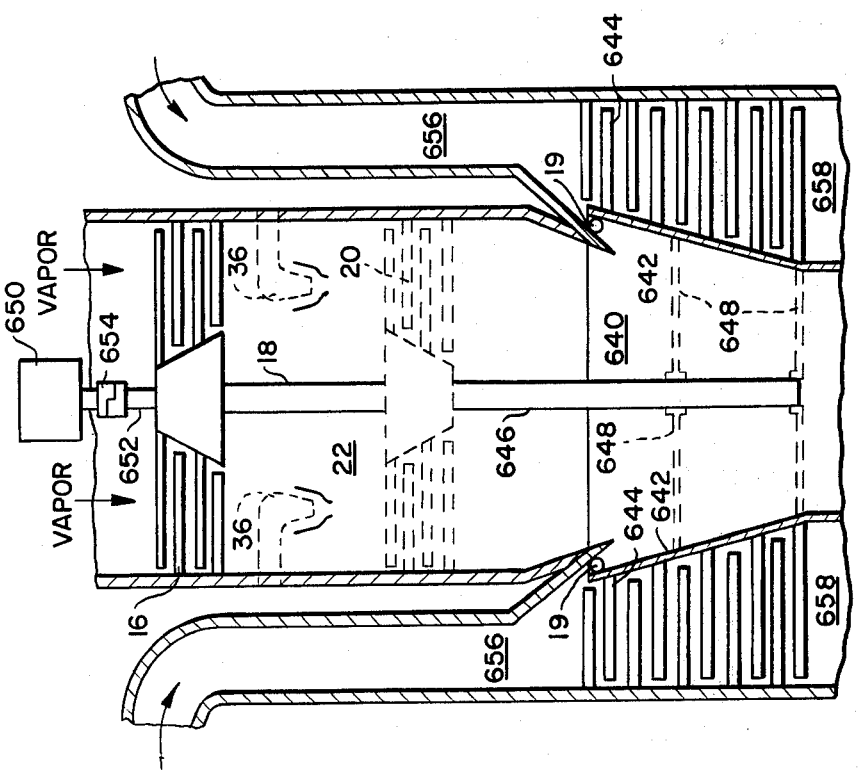
FIG. 6 illustrates schematically two turbines, one of which can be powered by dirty, hot gases, operating a turbine compressor as an optional turbine-compressor unit useful in the many embodiments of the present invention.

FIGS. 6 and 7 illustrate embodiments of the compressor-turbine combination which permit the use of hot, dirty combustion gases (or, if the apparatus is appropriately designed, a fluid such as water) to provide additional motive power for driving the turbine and, in turn, through the linked shaft, for driving the vapor compressor as well. In these embodiments, the hot, dirty combustion gases do not actually mix with the vapor in the system, and, therefore, the purity of the condensate produced by the system is not compromised by use of dirty combustion gases for additional motive power. Referring first to FIG. 6 there is shown a configuration which includes the conventional compressor-turbine combination and a mixing chamber for mixing hot, clean combustion gases with the vapor flowing through the turbine and the compressor. In addition, the unit illustrated in FIG. 6 includes a hot, dirty combustion gas driven turbine which increases the shaft power available for driving the compressor. The unit of FIG. 6 includes compressor 16 linked through shaft 18 to optimal turbine 20 and vapor-combustion gas mixing chamber 22 defining the space between the turbine and the compressor. Injectors 36 emit hot, clean combustion gases for mixing the vapor with the result that the combined flow of the vapor and the combustion gases operate turbine 20, which, through shaft 18, drives compressor 16. The system also includes a dirty combustion gas operated turbine 640 which consists essentially of a hollow spindle 642 and blades 644 attached to the outside surface of the hollow spindle. The spindle 642 is drivingly linked to shaft 646 through supports 648. Shaft 646 is operatively linked with the spindle of turbine 20 which spindle is joined through shaft 18 to the spindle of compressor 16. In operation, the system is energized by starting motor 650 acting through shaft extension 652 and clutch 654. Dirty combustion gas turbine 640 is disposed with its blades arranged in flow space 656 which is annularly arranged with respect to vapor and clean combustion gas flow space 22 and which is separated therefrom by a solid partition and sealing ring 19. In this manner, hot dirty combustion gases are directed through space 656 to act on turbine blades 644 which, through spindle 642 and supports 648, rotate shaft 646. The expanded dirty combustion gases exhaust from the turbine 640 into space 638 in such a manner that they never combine or mix with the vapor or the clean combustion gases. Shaft 646 may be operatively linked with the spindle of compressor 16 when turbine 20 is not employed and with the spindle of compressor 24 (not shown) whether or not turbine 20 is employed.

FIG. 7 illustrates a completely concentric unit wherein one compressor-mixing chamber-turbine combination surrounds and is directly linked to another compressor-mixing chamber-turbine combination. In this configuration, the outer compressor-mixing chamber-turbine combination supplies rotatry power to the inner system to improve the performance of the inner system. The inner system, which is the compressor-mixing chamber-turbine combination disclosed in FIGS. 1, 1A, and 1B, includes compressor 16 linked through shaft 18 to turbine motor 20 and mixing chamber 22 between the compressor and the turbine in which clean combustion gases emitting from injectors 36 admix with the vapor flowing through chamber 22 to operate turbine 20. Extending from the spindle of compressor 16 and from the spindle of turbine 20 are shaft members 700 and 702 respectively. Connected to shaft 702 are supports 704 which rotate compressor 706 through its hollow spindle 708. Connected to shaft 700 are supports 710 through which shaft 700 is rotated by the hollow spindle 712 of turbine 714. The blades 707 of compressor 706 and 713 of turbine 714 are arranged in an annular space surrounding the compressor-turbine unit 16, 20. The annular space is separated from the vapor clean combustion gas flow space by a solid partition and sealing ring 19. Turbine 714 is operated by combustion gases, which may be dirty gases, emitted into space 716 through injectors 718. In space 716 the combustion gases may be mixed with air drawn therein from space 720 upstream of compressor 706 which air is drawn into the system and compressed by compressor 706. The air admixed with the hot combustion gases exhausts through space 722 and never comes in contact with the vapor and clean combustion gases which move through space 22. As the dirty combustion gases and air drawn in through space 716 pass through turbine 714, they do work on the turbine blades 713 causing turbine 714 to rotate and to transmit power through supports 710 to shaft 700, which power is utilized by coaxial compressor 16 in doing work on the vapors which are drawn into space 22. If desired, power could be transmitted by shaft 700 to operate independent compressor 24 (not shown). In an alternative form of this embodiment, space 716 may operate as a combustion chamber and injectors 718 used to inject fuel into the space for combustion with the air drawn in from space 702 to in situ produce combustion gas for operating compressors 16 and/or 24 and/or turbine 20.

Numerous modifications can be made to the configuration illustrated in FIG. 7 to alter it and/or improve it for particular usages. Thus, supports 704 and 710 could be formed into air foil shaped fans to assist in the movement of large masses of vapor. Still another modification involves clutching and gearing the outer compressor-turbine combination to the inner compressor-turbine combination in order that the rate of rotation of the latter could be varied with respect to the former. Another useful modification is the addition of further compressor-turbine combinations in concentric relationship to the two shown in FIG. 7, all with the purpose of increasing the motive power available for compression in compressor 16 (and/or compressor 24) and of utilizing available energy sources, such as dirty combustion gases, in as economical manner as is possible. The fundamental advantage of the configuration of FIG. 7 is that it enables utilization of as many different combustion gas sources as may be available at the system location for supplying economical power to compress the vapors flowing into space 22.

Figure 9:
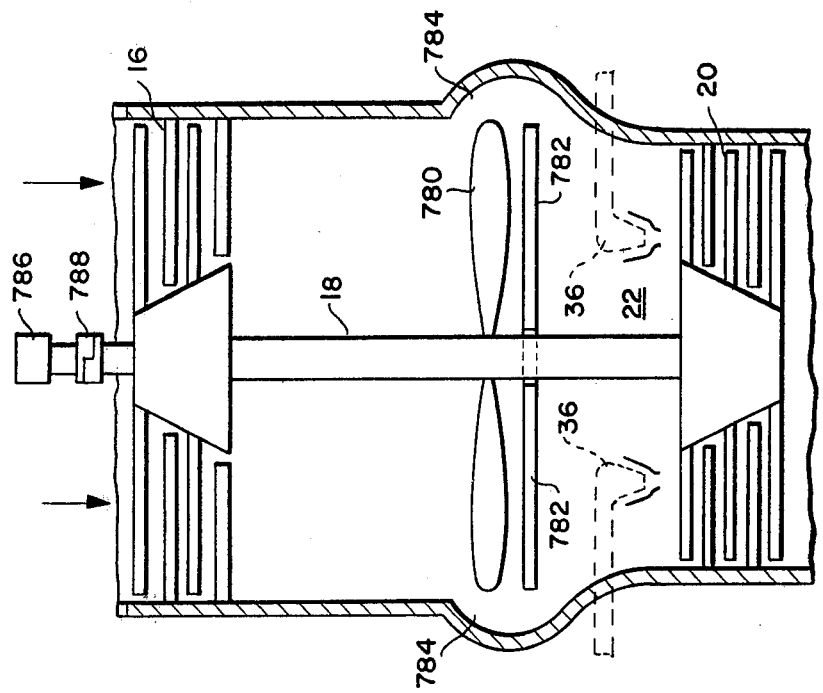
FIG. 9 illustrates schematically a centrifugal compressor and a turbine compressor operated by a single turbine motor as an optional turbine-compressor unit useful in the many embodiments of the present invention.
Figure 8:
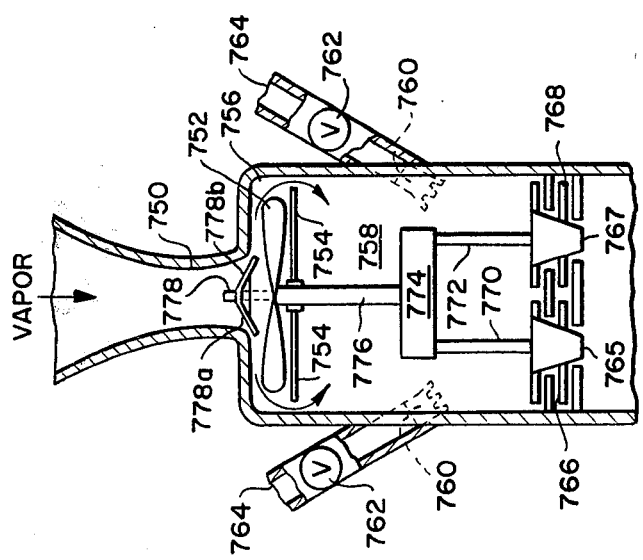
FIG. 8 illustrates schematically a centrifugal compressor operated by two turbine motors in tandem as an optional turbine-compressor unit useful in the many embodiments of the present invention.

FIGS. 8 and 9 show still other configurations for the compressor-mixing chamber-turbine unit of FIGS. 1, 1A and 1B. Specifically, these FIGS. 8 and 9 illustrate the use of centrifugal compressors instead of or in addition to turbine compressors. Centrifugal compressors have the advantage that they readily pass condensed liquid via the large waterways at the tips of the compressors impellers. Referring first to FIG. 8, there is shown an inlet nozzle which leads from the evaporative unit directly to the impeller of a centrifugal compressor. Nozzle 750, which is optionally a venturi nozzle but may be merely an inlet duct, directs the hot vapor to impeller 752 of a centrifugal compressor which includes back plates 754 to prevent the flow of vapor straight through and to assist impeller 752 in directing and concentrating the flow of vapor toward the sides 756 of the chamber off the tips of the impeller. The compressed vapor passing centrifugal impeller 752 flows past back plates 754 and into space 758 where it mixes with hot, clean combustion gases issuing from injectors 760 which are shown in FIG. 8 to be optional multi-nozzle injectors. The flow of combustion gases through injectors 760 is controlled by flow valves 762 disposed in the arms 764 leading to the injectors. The vapor passing the centrifugal compressor admixes with the combustion gases and together the vapor and gases motivate turbines 766 and 768 disposed in tandem. As spindles 765 and 767 of turbines 766 and 768 are caused to rotate, they in turn rotate shafts 770 and 772 linked through clutch and transmission box 774 to shaft 776. Rotation of shaft 776 operates impeller 752 of the centrifugal compressor. As in the other configurations disclosed herein, the system can be started rotating initially utilizing a starter motor through a clutched system shaft-linked to one of the spindles 765, 767 of the tandem turbines. Optional butterfly valve 778 is shown disposed in the neck of entrance nozzle 750 to control the flow direction of the vapors entering from the boiler. The butterfly valve 778 is preferably arranged in such a manner that arms 778a and 778b can be brought together to fully open nozzle 750 and, in that position, to offer little or no resistance to vapor flow therethrough.

FIG. 9 illustrates turbine compressor 16 shaft linked through shaft 18 to turbine motor 20 and clean combustion gas injectors 36 disposed in mixing chamber 22 to emit clean combustion gases for combination with the vapor flowing through compressor 16 to conjointly operate turbine 20. Starting motor 786 and clutch 788 are provided for initial start-up of the system. In this embodiment, however, a centrifugal impeller 780 is operated by shaft 18 in conjunction with back plates 782. As described in connection with FIG. 8, the impeller together with the back plates directs and concentrates the flow of vapor toward the ends of the impeller into spaces designated generally as 784 whereupon the vapors are additionally compressed prior to admixing in space 22 with the clean combustion gases emitting from injectors 36.

Figure 10:
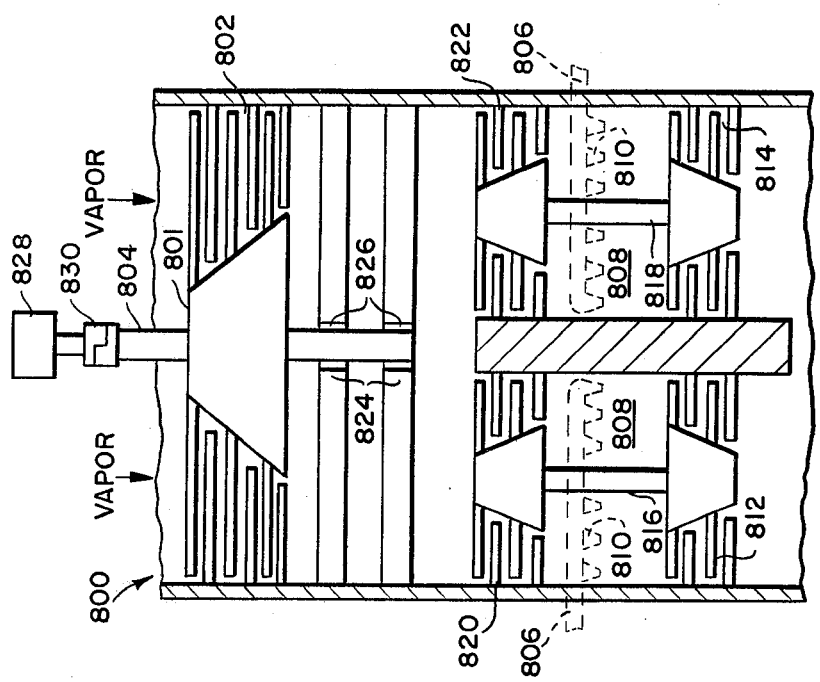
FIG. 10 illustrates schematically an optional free wheeling compressor unit with two turbine driven compressors in tandem, which unit is useful as the turbine-compressor unit in the many embodiments of the present invention.

Yet another useful configuration for the compressor-mixing chamber-turbine unit is illustrated generally at 800 in FIG. 10. The unit shown consists of two compressor-turbine combinations in tandem combinations. Specifically, free-wheeling compressor 802 is disposed in the path of vapor entering the unit and permitted to rotate at its own rate which is dependent only on the flow rate of vapor therethrough. Starter motor 828 and clutch 830 are shown operating on shaft 804 to which spindle 801 of the free-wheeling compressor is also connected. Hot clean combustion gases enter the system through feed lines 806 and are emitted into mixing chamber 808 of each tandem unit through injectors 810 therein. The hot, clean combustion gases admix with the vapor flowing through chambers 808 and the vapor and gases together operate on turbines 812 and 814. Turbines 812, 814 are linked respectively, through shafts 816, 818 to compressors 820, 822, which compressors are operated by rotation of turbines 812 and 814. As compressors 820 and 822 are rotated, vapor is drawn into the unit past free-wheeling compressor 802 causing the latter compressor to rotate while supported by supports 824 and bearings 826. The configuration of FIG. 10 has the obvious advantage of affording a larger through-put while utilizing less power due to the presence of the free-wheeling compressor 802. Depending upon the motive power necessary for compression in the system, either or both of turbines 812 and 814 can be used.

The various embodiments of the present invention are particularly applicable to the fractional distillation of binary mixtures such as $EtOH-H_2O$ to recover substantially anhydrous EtOH as the low boiling component of the mixture. It is evident from the background discussion presented earlier herein that present methods for manufacturing substantially anhydrous EtOH are grossly impractical in the great number of steps needed to produxe a "beer" starting material from other than a petrochemical source and in the necessity to employ petrochemical and energy intensive processes to produce anhydrous EtOH, even from a non-petrochemical "beer" starting material. The prior art beer still, aldehyde column, fusel oil column and rectifying column used to make the 95.6 wt % EtOH mixture and the benzene ternary azeotrope distillation or glycerine-/ethylene glycol counter current extraction processes may advantageously be replaced by the systems illustrated in FIGS. 1, 1A and/or 1B hereof. Use of the present methods permits the fractional distillation of relatively inexpensive, dilute EtOH-water mixtures derivable from plentiful sources under partial vacuum below 100 mm Hg at which pressure the $EtOH-H_2O$ azeotrope disappears. The result, after EtOH vapors are processed in the vapor treatment portion of the present system, is to produce a distillate of anhydrous EtOH and flammable low boilers, all of which will burn as fuel. The residue comprises water and all components of fusel oils that boil above water at the partial vacuum pressure chosen. For example, if 1,000 gallons of 10% by weight EtOH "beer" solution is fractionally distilled under vacuum, it will produce 100 gallons anhydrous EtOH mixed with about one gallon of aldehydes and a residue of 898 gallons of water mixed with about one gallon of high boiling fusel oils. It is clear that the residue is so diluted that it poses no danger to the environment. Furthermore the high boiling fusel oils are biodegradable, allowing the residue to either be run to waste or the water separated out by further fractional distillation and re-used. In the latter case, the residue will be high boiling fusel oils which can be cracked to produce other chemicals or burned to produce discardable products such as carbon dioxide and water. Production of anhydrous or gasohol grade EtOH by the process and using the system of the present invention results in considerable savings over prior processes in terms of capital energy and resource expenditures in that there is no need for cooling water for condensation, petrochemicals, steam or electricity and there is a decrease in capital equipment needs.

Particularly pertinent to the economics of the present process is the provision of an inexpensive source of EtOH for processing, such as a convertible chemical stream or a "beer" solution. Presently there are three methods for making ethyl alcohol, as follows:
1. Synthesis with ethylene by hydration;
2. Fermentation of plant products or sugar solutions;
3. Enzymatic conversion of plant products or sugar solutions.

Although the first method is presently the most often used, for all practical purposes it cannot be relied upon as a source of anhydrous EtOH in the large quantities required to make gasohol. This is because ethylene is a crude oil derivative and, as such, has become prohibitively costly.

The second and third methods are similar and rely upon the conversion of sucrose to invert sugar and invert sugar to ethyl alcohol. Among the most useful enzymes employed are invertase and zymase. The chemical relationship between the starting material sucrose and the EtOH product dictates that 1.4239 pounds of sucrose are needed per pound of ethyl alcohol produced or, converting to gallons of alcohol, 9.3204 pounds of sugar are required per gallon of ethyl alcohol. Thus, it can be seen that the production of ethyl alcohol by fermentation or enzymatic conversion is material intensive and largely impractical from that standpoint. To become practical requires that a source of sugar be identified that is neither material nor cost intensive.

It is believed that the best raw material source for the production of anhydrous ethyl alcohol is honey produced by bees. This is because honey can be more than 70% sugar and thus a rich source of sugar and, in the manner hereinafter explained, honey can be relatively inexpensively produced in large quantities using controlled environments and then harvested in an automated fashion. The large amounts of honey serve as a source of sugar for producing dilute ethyl alcohol-water "beer" solutions which can serve as the raw feed to the systems of FIGS. 1, 1A and 1B.

There are many reasons why honey is particularly advantageous as a raw material for ethyl alcohol production. First, it is readily available since it can be obtained from a huge variety of flowers and plants and flowers and plants can readily be genetically rearranged to produce honey with the least undesirable by-products for EtOH production. Honey has a low insoluble solids content and will, therefore, produce decreased slop or mash residue. Additionally, honey contains only a very small percentage of substances that boil below EtOH. Honey readily lends itself to continuous distillation processing and will react by fermentation mechanisms to produce enzymes which are useful to produce EtOH enzymatically from the honey. Moreover the production of EtOH enzymatically with honey, at pressures and temperatures under which no EtOH-$H_2O$ azeotrope exists, will result in the highest purity EtOH obtainable in a single pass through vacuum distillation apparatus.

Figure 11:
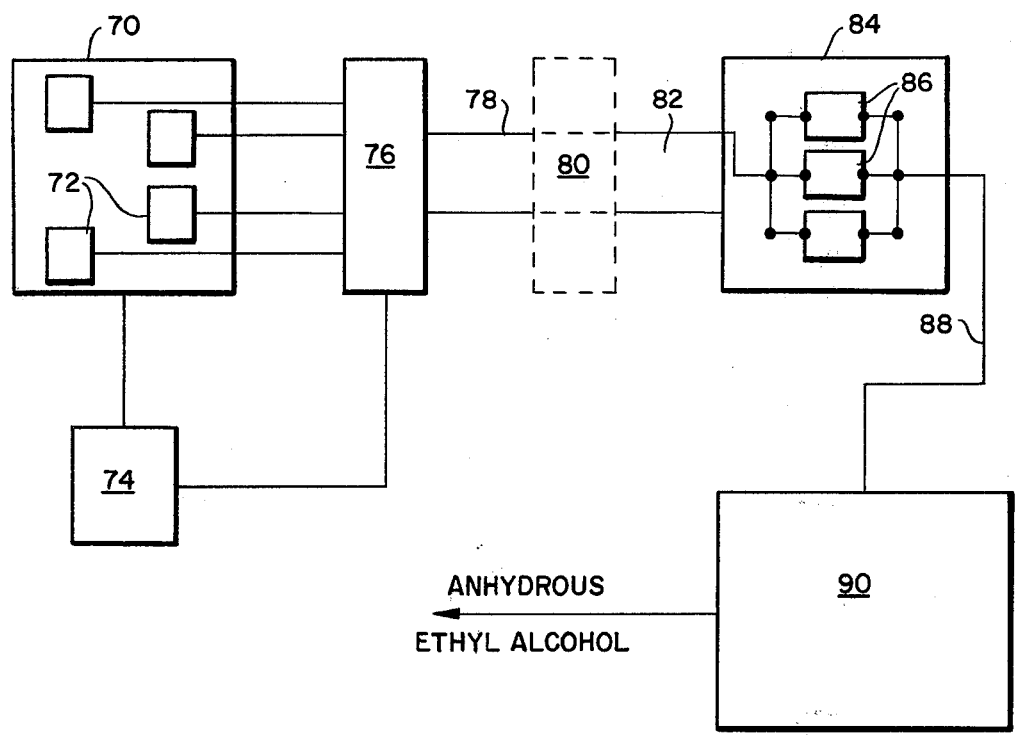
FIG. 11 illustrates in block diagram from a system for producing and collecting large quantities of honey and for converting the honey to anhydrous ethyl alcohol.

Referring to FIG. 11 there is shown in block diagram format a system and method for producing, automatically harvesting and using honey as the raw material in the production of substantially anhydrous ethyl alcohol. A honey production facility 70 containing a plurality of environmental buildings 72 is provided for encouraging maximum honey production. The temperature, pressure, lighting and other relevant environmental conditions are controlled within the buildings 72 to provide the most favorable conditions, year around, for plant growth and for the general well being of the bees and hives within the buildings. It is known that bees typically produce the most honey during the summer months. Therefore, honey production per hive could be maximized by maintaining a summer-like environment within buildings 72 all year. Environmental conditions within the buildings 72 are monitored in control center 74 located outside of buildings 72 using sensors within the buildings which sense environmental indicia and send signals to control center 74. From center 74 command signals may be sent to automatic control means, such as thermostats, artificial lighting, etc. for adjusting environmental conditions within predetermined limits. The hives include sensors which indicate by signal when it is time to empty the hives of their honey. Such sensors might include, for example, hive weight sensors which detect the increase in hive weight due to increased honey content and which either signal control center 74 or signal and by automatically sent command initiate honey removal from the honeycomb. Automatic honey harvesting means 76, such as compressed air jets which blow the honey from the hives into appropriate collection means, can be actuated by a signal sent from control center 74 based upon a sensor indication received at center 74 from buildings 72. For example, the honey could be blown into collection conduits 78 or onto conveyors and pumped or transported to a sugar production facility 80 at which the sugar component of the honey is separated and placed in a form suitable for conversion in conversion center 84 to ethyl alcohol and water by fermentation and/or enzymatic conversion. Since honey is often viscous it may be necessary to treat it to improve its flow and/or other properties prior to conveying or converting it. Depending on the raw honey available, it may be necessary to treat it by heating, diluting, adding nutrients, or the like, in order to optimize the fermentation or enzymatic reactions. In a preferred system the honey is sent directly to the conversion center to serve as the raw material for ethyl alcohol production. Either the sugar component from facility 80 or the raw honey from harvesting means 76 and collection conduit 78 is ducted via conduit 82 to conversion center 84. The latter may include a plurality of holding tanks 86 where fermentation under anerobic conditions takes place by conventional fermentation processes to convert the sugar to ethyl alcohol-water mixtures containing about 6–12% by weight EtOH. Holding tanks 86 are periodically emptied into pipeline 88 which carries the EtOH-water mixture to the fractional distillation and EtOH vapor treatment unit 90. The 6–12% EtOH/$H_2O$ mixture serves as the raw feed entering feed line 102 of any of the systems illustrated in FIGS. 1, 1A or 1B hereof. The low boiling anhydrous EtOH is purified, as previously described, and exits the systems of FIGS. 1, 1A or 1B through discharge conduit 112 and valve 113 for collection and eventual use.

Figure 12:
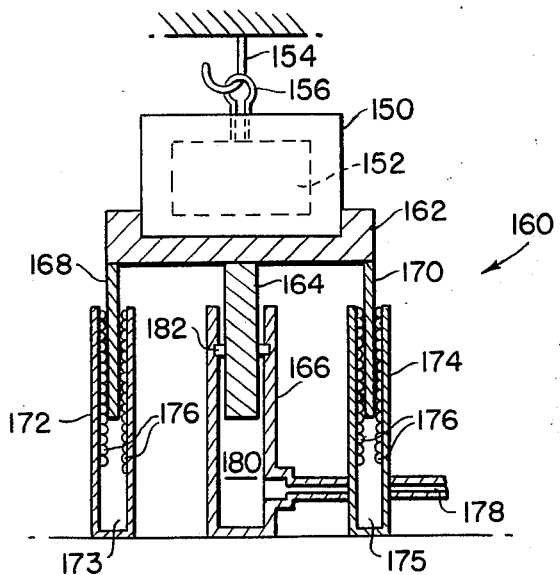
FIG. 12 illustrates schematically exemplary means for sensing honey production and for honeycomb removal from the hives.

Referring to FIG. 12 there is shown schematically an exemplary means 160 for supporting a hive 150 within environmental buildings 72, for sensing hive weight increase due to increased honey content and for removal of honey bearing honeycomb plates 152 from the hive in preparation for harvesting. More specifically, means 160 includes a hive platform 162 supported by piston 164 which is slidable within hydraulic cylinder 166 for free vertical movement between predetermined upper and lower limits. Supports 168,170, providing lateral support for platform 162, are slidable within guide cylinders 172,174, respectively. A plurality of ball bearings 176 project radially from the cylinder wall into the cavities 173,175 of guide cylinders 172,174, respectively, to facilitate free vertical movement of supports 168,170 therein. Piston 164 is vertically slidable within cylinder 166 by introducing hydraulic fluid through conduit 178 into cylinder cavity 180, the upper limit of which is defined by piston seal 182. By increasing hydraulic pressure within cavity 180, piston 164 can be made to slide vertically upwardly within cylinder 166. On the other hand, by decreasing hydraulic pressure within cavity 180, piston 164 can be made to move downwardly within cylinder 166. In this manner, hive 150 can be moved up or down relative to honeycomb plate 152 whose vertical position can be fixed by hook means 154 extending through and engaging eyelet 156 of the honeycomb plate 152.

In normal operation of honey production facility 70, hive 150 (which is exemplary of the many hives within the facility), including honeycomb plates 152, is supported by and in equlibrium with the hydraulic pressure within cavity 180 acting upon piston 164. The vertical position of hive 150 is adjusted by adjusting hydraulic pressure so that the honeycomb plates are supported by hive 150 but engage hook means 154 via eyelet 156. It will be appreciated that the weight of hive 150 and its contents is directly proportional to the hydraulic pressure within cavity 180 and this pressure can be measured by transducers (not shown) well known in the art, such as piezo-electric pressure transducers, bourden gauges, manometers, and the like. Thus, the weight of the hive plus its contents can be measured by calibrating the hydraulic pressure against a known weight. As the weight of the hive plus its contents increases, due to the production of honey, this weight increase can be monitored by monitoring the increase in hydraulic pressure and, at the appropriate moment, a hive emptying signal can be automatically or manually sent to initiate the sequence of honeycomb removal from the hives and honey removal and recovery from the honeycombs.

Honeycomb removal from the hives is readily accomplished by decreasing hydraulic pressure within cavity 180 to cause piston 164 to slide downwardly within cylinder 166. As this occurs, hive platform 162 and hive 150 supported thereon also move downwardly until eyelet 156 fully engages hook means 154 and support of the weight of the honeycomb plates 152 shifts from hive 150 to hook means 254. Hydraulic pressure within cavity 180 continues to be decreased until hive 150 is lowered sufficiently that honeycomb plates 152 are completely removed therefrom.

Figure 13:
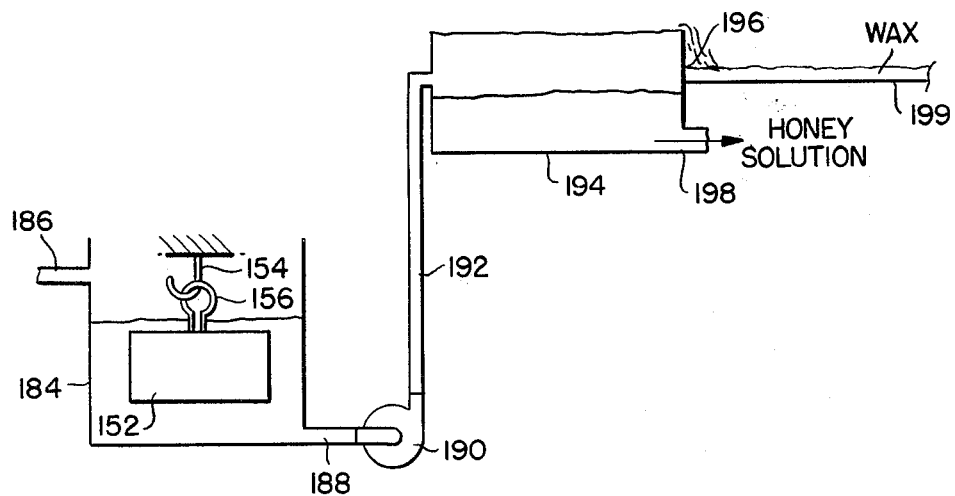
FIG. 13 illustrates schematically exemplary means for honey removal and recovery from the honeycombs.

Referring to FIG. 13 there is schematically shown means for honey removal and recovery from the honeycomb plates 152. Trough 184 is filled with hot water via feed line 186 and the honeycomb plates 152 removed from hive 150 are immersed therein for a time sufficient to dissolve the honey and melt the wax on the honeycomb plates 152. Desirably, plates 152 are suspended from hook 154 which is associated with a conventional hook and conveyor system well known in the art. After the honey is dissolved and the wax melted, the honeycomb plates 152 are removed from trough 184, blown dry, and returned to hive 150. The wax and honey solution in hot water is pumped via line 188 by pump 190 into line 192 which empties into tank 194. Tank 194 contains a weir 196 having an opening 198 and a septum 199. The wax floats on the honey solution and overflows weir 196 onto septum 199 from which it is collected, washed and sold as a byproduct of the honey production process. The heavier honey solution exits tank 194 via opening 198 and is subsequently pumped to the fermentation tanks of conversion center 86 for conversion to a 6–12% beer solution. The beer serves as the raw feed for the fractional distillation and vapor treatment systems of any of the embodiments hereof to obain substantially anhydrous EtOH.

Another optional method for separating honey from the honeycomb plate is to place the plate in a centrifuge, well-known in the art, to remove honey, but not wax, from the honeycomb. The honeycomb plate, freed of honey but still containing the wax, may then be returned to the hive. This procedure avoids the need for the bees to produce wax and increases the production rate of honey. The honey then can be diluted with water, as stated above, and pumped to the fermentation tanks without any need to separate the wax.

While the present invention has been described with reference to particular embodiments thereof, it will be understood that numerous modifications can be made by those skilled in the art without actually departing from the scope of the invention. Accordingly, all modifications and equivalents may be resorted to which fall within the scope of the invention as claimed.

We claim:
1. A method for high volume distillation of impure liquids comprising the steps of:
   (a) evaporating said impure liquid in a fractional distillation evaporator to separate a low boiling component vapor from said liquid;
   (b) compressing said vapor to a predetermined pressure;
   (c) reacting at least a portion of said compressed vapor at said predetermined pressure in the vapor phase in a catalyst-containing reaction zone for producing an adjusted composition vapor;
   (d) compressing said vapor exiting said reaction zone to form a recompressed vapor at a predetermined pressure corresponding to a predetermined temperature differential between said recompressed vapor and said impure liquid;
   (e) adding sufficient energy to operate said compression steps;
   (f) cooling said recompressed vapor in heat transfer relation with said impure liquid whereby said recompressed vapor at least partially condenses, transferring heat to said impure liquid for fractionally distilling said liquid and separating said low boiling component vapor; and
   (g) collecting said condensed low boiling component.

2. A method, as claimed in claim 1, further including the step of passing at least a portion of said compressed vapor exiting said adjustment zone through a means for expanding said vapor to produce at least a portion of the energy for operating said compression steps.

3. A method, as claimed in claim 1, wherein said portion of said compressed vapor passed through said zone comprises from 0.001 to 100% by volume of said compressed vapor flow; and, said vapor from said zone is compressed by bypassing said zone with the remainder of said compressed vapor and admixing said remainder at a pressure at least equal to said predetermined pressure directly with said vapor from said zone to compress said vapor from said zone and to expand said compressed vapor to form a second vapor at least at ambient pressure and at a temperature corresponding thereto, said temperature and pressure of said second vapor being greater than that of the vapor exiting said zone and less than that of the remainder of said compressed vapor prior to admixing, said second vapor passing to said step for forming said recompressed vapor.

4. A method, as claimed in claim 2, wherein said portion of said compressed vapor passed through said zone and said expansion means comprises from 0.001 to 100% by volume of said compressed vapor flow; and, said expanded vapor from said zone and expansion engine is compressed by bypassing said zone and expansion engine with the remainder of said compressed vapor and admixing said remainder at a pressure at least equal to said predetermined pressure directly with said expanded vapor to compress said expanded vapor and to expand said compressed vapor to form a second vapor at least at ambient pressure and at a temperature corresponding thereto, said temperature and pressure of said second vapor being greater than that of the expanded vapor exiting said zone and expansion engine and less than that of the remainder of said compressed vapor prior to admixing, said second vapor passing to said step for forming said recompressed vapor.

5. A method, as claimed in claim 4, wherein a portion of said compressed vapor bypassing said expansion engine is admixed with said recompressed vapor to form a third vapor at ambient pressure and a temperature corresponding thereto, and said third vapor is passed in heat transfer relationship with said impure liquid.

6. A method, as claimed in claims 1, 2, 3, 4 or 5 wherein said vapor undergoes a chemical reaction in said zone.

7. A method, as claimed in claims 1, 2, 3, 4 or 5 wherein the ratio of vapor pressure of said vapor following said first compression step to the vapor pressure of said low boiling component is in the range 1.2:1 to 250:1.

8. A method, as claimed in claim 7, wherein the ratio is in the range 5:1 to 100:1.

9. A method, as claimed in claims 2, 4 or 5, wherein shaft energy produced by said vapor in said expansion engine comprises at least a portion of the energy to operate said compression steps.

10. A method, as claimed in claims 1, 2, 3, 4 or 5, wherein said condensation of vapor occurs in said evaporator and said released heat is transferred to said impure liquid in said evaporator to evaporate said liquid.

11. A method, as claimed in claims 1, 2, 3, 4 or 5, wherein said condensation of vapor occurs in a heat exchanger and said released heat is transferred to said impure liquid before said liquid enters said evaporator.

12. A method, as claimed in claims 1, 2, 3, 4 or 5, wherein said compressions and expansions are substantially adiabatic.

13. A method, as claimed in claims 1, 2, 3, 4 or 5, wherein at least a portion of said energy to operate said compression steps is added by driving compression means with an external mechanical energy source.

14. A method, as claimed in claims 1, 2, 3, 4 or 5, including the step of diverting a fraction of said vapor to be cooled in heat transfer relation with said impure liquid and mixing said diverted vapor fraction directly with said impure liquid, whereby said vapor condenses and said impure liquid is heated.

15. A method, as claimed in claims 1, 2, 3, 4 or 5, including the step of diverting a fraction of said compressed vapor and admixing said diverted fraction directly with said impure liquid, whereby said vapor condenses and said impure liquid is heated.

16. A method, as claimed in claim 15, wherein said diverted fraction is injected into said impure liquid upstream of said evaporator.

17. A method, as claimed in claims 1, 2, 3, 4 or 5, wherein said low boiling component is evaporated at a temperature below its boiling point at ambient pressure.

18. A method, as claimed in claims 2, 4 or 5, wherein at least a portion of said energy to operate said compression steps is added to said expansion engine by admixing said portion of said compressed vapor directly with hot gases having a temperature sufficiently greater than the temperature of said compressed vapor to increase the temperature of said compressed vapor and passing said heated vapor through said expansion engine to motivate said engine.

19. A method, as claimed in claim 18, wherein said compressed vapor is admixed with hot clean combustion gases.

20. A method, as claimed in claims 1, 2, 3, 4 or 5, wherein at least a portion of said energy to operate said compression steps is added by passing a hot gas through a space separate from the space in which said vapor flows, said hot gas comprising a gas other than the vapor produced in step (a) and passing through a means for expanding said gas.

21. A method, as claimed in claim 20, including the steps of drawing air through said hot gas flow space for mixing with said hot gas flow therein, passing said air through means for compressing said air prior to mixing with said hot gas flow, and drivingly linking said hot gas expanding means in said hot gas flow space with said air compressing means in said hot gas flow space, whereby at least a part of the energy produced by expanding said hot gas flow is used to operate said air compressing means.

22. A method, as claimed in claim 21, further including the steps of admitting fuel into said hot gas flow space upstream of said hot gas expanding means and igniting said fuel, whereby said hot gas flow is produced in said space.

23. A method, as claimed in claim 20, wherein said hot gas flow space is annularly disposed with respect to the space in which said vapor flows.

24. A method, as claimed in claim 21, wherein said hot gas flow space is annularly disposed with respect to the space in which said vapor flows.

25. A method for high volume distillation of impure liquid comprising the steps of:
(a) evaporating said impure liquid in a fractional distillation evaporator to separate a low boiling component vapor;
(b) compressing said vapor to a predetermined pressure;
(c) reacting at least a portion of said compressed vapor at said predetermined pressure in the vapor phase in a catalyst-containing reaction zone for producing an adjusted composition vapor;
(d) passing said vapor exiting said reaction zone through an expansion engine, said vapor doing work on said engine to motivate said engine and to produce shaft energy, whereby said vapor expands and cools, said portion comprising from 0.001 to 99.999% by volume of said compressed gas flow;

(e) adding make-up work to said expansion engine to supplement the work done on said engine by said vapor expanding therethrough, said added work being sufficient to at least make-up the difference between the work done in compressing said vapor and the work done on said engine by said vapor in expanding therethrough;

(f) admixing the remainder of said compressed vapor at a pressure at least equal to said predetermined pressure directly with said expanded vapor to expand said compressed vapor and compress said expanded vapor to form a second vapor at ambient pressure and at a temperature corresponding thereto, said temperature and pressure of said second vapor being greater than that of the expanded vapor exiting said expansion engine and less than that of the remainder of the compressed vapor prior to admixing;

(g) cooling said second vapor in heat transfer relation with said impure liquid whereby said second vapor at least partially condenses, transferring heat to said impure liquid for fractionally distilling said liquid and separating said low boiling component vapor; and (h) collecting said condensed low boiling component.

26. A method, as claimed in claim 25, wherein said vapor undergoes a chemical reaction in said zone.

27. A method, as claimed in claim 25, wherein the ratio of vapor pressure of said vapor following said first compression step to the vapor pressure of said low boiling component is in the range 1.2:1 to 250:1.

28. A method, as claimed in claim 27, wherein the ratio is in the range 5:1 to 100:1.

29. A method, as claimed in claim 25, wherein shaft energy produced by said vapor in said expansion engine comprises at least a portion of the energy to operate said compression step.

30. A method, as claimed in claim 25, wherein said condensation of vapor occurs in said evaporator and said released heat is transferred to said impure liquid in said evaporator to evaporate said liquid.

31. A method, as claimed in claim 25, wherein said condensation of vapor occurs in a heat exchanger and said released heat is transferred to said impure liquid before said liquid enters said evaporator.

32. A method, as claimed in claim 25, wherein said compressions and expansions are substantially adiabatic.

33. A method, as claimed in claim 25, wherein at least a portion of said energy to operate said compression step is added by driving compression means with an external mechanical energy source.

34. A method, as claimed in claim 25, including the step of diverting a fraction of said vapor to be cooled in heat transfer relation with said impure liquid and mixing said diverted vapor fraction directly with said impure liquid, whereby said vapor condenses and said impure liquid is heated.

35. A method, as claimed in claim 25, including the step of diverting a fraction of said compressed vapor and admixing said diverted fraction directly with said impure liquid, whereby said vapor condenses and said impure liquid is heated.

36. A method, as claimed in claim 35, wherein said diverted fraction is injected into said impure liquid upstream of said evaporator.

37. A method, as claimed in claim 25, wherein said low boiling component is evaporated at a temperature below its boiling point at ambient pressure.

38. A method, as claimed in claim 25, wherein at least a portion of said energy to operate said compression step is added to said expansion engine by admixing said portion of said compressed vapor directly with hot gases having a temperature sufficiently greater than the temperature of said compressed vapor to increase the temperature of said compressed vapor and passing said heated vapor through said expansion engine to motivate said engine.

39. A method, as claimed in claim 38, wherein said compressed vapor is admixed with hot clean combustion gases.

40. A method, as claimed in claim 25, wherein at least a portion of said energy to operate said compression step is added by passing a hot gas through a space separate from the space in which said vapor flows, said hot gas comprising a gas other than the vapor produced in step (a) and passing through a means for expanding said gas.

41. A method, as claimed in claim 40, including the steps of drawing air through said hot gas flow space for mixing with said hot gas flow therein, passing said air through means for compressing said air prior to mixing with said hot gas flow, and drivingly linking said hot gas expanding means in said hot gas flow space with said air compressing means in said hot gas flow space, whereby at least a part of the energy produced by expanding said hot gas flow is used to operate said air compressing means.

42. A method, as claimed in claim 41, further including the steps of admitting fuel into said hot gas flow space upstream of said hot gas expanding means and igniting said fuel, whereby said hot gas flow is produced in said space.

43. A method, as claimed in claim 40, wherein said hot gas flow space is annularly disposed with respect to the space in which said vapor flows.

44. A method, as claimed in claim 41, wherein said hot gas flow space is annularly disposed with respect to the space in which said vapor flows.

45. A system for high volume distillation of impure liquids comprising:

(a) fractional distillation evaporator means, including means for supplying impure liquid feed thereto, for separating a low boiling component vapor from said liquid;

(b) first compressor means receiving said vapor from said evaporator means for increasing said vapor pressure and temperature to predetermined pressure and temperature levels;

(c) a vapor composition adjustment zone including removably insertable catalyst means therein for receiving at least a portion of said compressed vapor from said first compressor means, said zone including vapor flow space wherein said vapor composition is catalytically altered or stabilized;

(d) second compressor means receiving the vapor exhausting said adjustment zone for increasing the vapor pressure and temperature thereof;

(e) means for driving said first and second compressor means;

(f) condenser means in heat transfer relationship with said impure liquid feed for receiving said vapor from said compressor means and for at least partially condensing said vapor whereby the heat released by said vapor is transferred to said feed liquid to supply heat energy for fractionally distilling said liquid and separating said low boiling component vapor;

(g) means for recovering condensed low boiling component from said condenser means; and (h) means for removing the remainder of said liquid feed from said evaporator means.

46. A system, as claimed in claim 45, further including expansion engine means motivated at least in part by compressed vapor from said adjustment zone and means for supplying make-up work to said expansion engine means, said engine being drivingly connected to said first compressor means whereby the work done by said vapor in expanding in said expansion engine means is transmitted to said first compressor means, said make-up supplementing the work done on said engine by said vapor expanding therethrough, said vapor exiting said engine means being directed to said second compressor means.

47. A system, as claimed in claim 45, further including a first mixing chamber for receiving said vapor exhausting from said adjustment zone and by-pass duct means for diverting the remainder of said compressed vapor from said first compressor means around said adjustment zone to said first mixing chamber, said remainder of said compressed vapor at a pressure at least substantially equal to said predetermined pressure admixing with and transferrting heat directly to said vapor exiting said adjustment zone to form a second vapor, whereby said compressed vapor is expanded and said vapor exiting said adjustment zone is compressed.

48. A system, as claimed in claim 46, further including a first mixing chamber for receiving said expanded vapor exhausting from said adjustment zone and expansion engine means and by-pass duct means for diverting the remainder of said compressed vapor from said first compressor means around said adjustment zone and expansion engine means to said first mixing chamber, said remainder of said compressed vapor at a pressure at least substantially equal to said predetermined pressure admixing with and transferring heat directly to said vapor exiting said adjustment zone and expansion engine means to form a second vapor, whereby said compressed vapor is expanded and said expanded vapor is compressed.

49. A system, as claimed in claim 48, further including a second mixing chamber downstream of said second compressor means for receiving compressed second vapor therefrom; second by-pass duct means for diverting a portion of said compressed vapor in said by-pass duct means around said first mixing chamber and said second compressor means to said second mixing chamber, said portion admixing with said compressed second vapor to form a third vapor; and, means for controlling the quantity of compressed vapor entering said first mixing chamber and said second mixing chamber.

50. A system, as claimed in claims 45, 46, 47, 48 or 49, wherein said means for driving said first and second compressors comprises at least in part a mechanical energy source and means drivingly linking said mechanical energy source to at least one of said compressors.

51. A system, as claimed in claims 45, 46, 47, 48 or 49, further including duct means upstream of said condenser means and communicating with said evaporator means for diverting a fraction of said vapor to be cooled in heat transfer relation with said impure liquid directly to said evaporator means for admixture with said impure liquid feed therein.

52. A system, as claimed in claims 45, 46, 47, 48 or 49, further including duct means downstream of said first compressor means for diverting a fraction of said compressed vapor directly to said means for supplying impure liquid feed to said evaporator means.

53. A system, as claimed in claim 52, wherein said means for supplying impure liquid feed includes a feed duct and said duct means downstream of said first compressor means includes a vapor injector means communicating with said feed duct to inject compressed vapor therein.

54. A system, as claimed in claims 47, 48, or 49, including means for controlling the portion of said compressed vapor flow diverted into said by-pass duct means.

55. A system, as claimed in claim 54, wherein said by-pass duct means include by-pass arms and vapor injector means at the end of said arms remote from said first compressor means, said vapor injector means injecting said by-pass vapor into said first mixing chamber.

56. A system, as claimed in claims 46, 48 or 49, wherein said means for supplying make-up work comprises a third mixing chamber for receiving said portion of said vapor from said first compressor means and means for supplying hot gases under pressure to said third mixing chamber, said hot gases admixing with and transferring heat directly to said vapor portion from said first compressor means in said third mixing chamber, and resulting heated vapor expanding through, doing work upon and motivating said expansion engine means.

57. A system, as claimed in claim 56, wherein said means for supplying hot gases comprises gas supply means and gas injector means, said gas injector means receiving gas from said gas supply means and injecting said gas into said third mixing chamber.

58. A system, as claimed in claim 56, wherein said expansion engine means is coaxial with said first compressor means and said third mixing chamber is disposed therebetween.

59. A system, as claimed in claims 45, 46, 47, 48 or 49, wherein said condenser means is disposed within said evaporator means in heat transfer relationship with said liquid feed in said evaporator means.

60. A system, as claimed in claims 45, 46, 47, 48 or 49, wherein said condenser means comprises heat exchange means disposed outside of said evaporator means.

61. A system as claimed in claims 45, 46, 47, 48 or 49, wherein said means for driving said first and second compressor means includes at least in part auxiliary turbine means drivingly connected to at least one of said compressor means, said auxiliary turbine means including a conduit for gas flow therethrough and turbine blading in said conduit, said turbine blading drivingly linked to at least one of said compressor means, whereby gas flow through said conduit does work on said turbine blading which work is transmitted to said compressor means.

62. A system, as claimed in claim 61, wherein said conduit is annularly disposed with respect to and separated from the space in which said vapor flows, said at least one compressor means is drivingly connected to said auxiliary turbine means through a shaft, and said auxiliary turbine means includes a spindle supporting said blading and drivingly connected to said shaft.

63. A system, as claimed in claim 62, wherein said auxiliary turbine spindle is hollow and said vapor flows therethrough.

64. A system, as claimed in claim 61, further including auxiliary compressor means in said conduit upstream of and drivingly connected to said auxiliary turbine means, said auxiliary compressor means drawing air through said conduit, whereby said air flow together with said gas flow in said conduit motivates said auxiliary turbine means.

65. A system, as claimed in claim 62, including auxiliary compressor means disposed in said annular conduit, said auxiliary compressor means drivingly connected to said auxiliary turbine means through said shaft and including a spindle supporting compressor blading in said conduit.

66. A system, as claimed in claim 65, wherein said compressor spindle is hollow and said vapor flows through said spindle.

67. A system, as claimed in claims 45, 46, 47, 48 or 49, wherein said first compressor means has a compression ratio in the range 1.2:1 to 250:1.

68. A system for high volume distillation of impure liquids comprising:
  (a) fractional distillation evaporator means, including means for supplying impure liquid feed thereto, for separating a low boiling component vapor from said liquid;
  (b) first compressor means receiving said vapor from said evaporator means for increasing said vapor pressure and temperature;
  (c) a vapor composition adjustment zone including removably insertable catalyst means for receiving at least a portion of said vapor from said first compressor means, said zone including vapor flow space wherein said vapor composition is catalytically altered or stabilized;
  (d) expansion engine means motivated at least in part by compressed vapor from said adjustment zone and means for supplying make-up work to said expansion engine means, said engine being drivingly connected to said first compressor means whereby the work done by said vapor in expanding in said expansion engine means is transmitted to said first compressor means, said make-up work supplementing the work done on said engine by said vapor expanding therethrough;
  (e) a first mixing chamber for receiving said expanded vapor exhausting from said expansion engine means and by-pass duct means for diverting the remainder of said compressed vapor from said first compressor means around said adjustment zone and said expansion engine means to said first mixing chamber, said remainder of said compressed vapor at a pressure at least substantially equal to said predetermined pressure admixing with and transferring heat directly to said vapor exiting said expansion engine means to form a second vapor, whereby said compressed vapor is expanded and said expanded vapor is compressed;
  (f) condenser means in heat transfer relationship with said impure liquid feed for receiving said second vapor from said first mixing chamber and for at least partially condensing said vapor whereby the heat released by said vapor is transferred to said feed liquid to supply heat energy for fractionally distilling said liquid and separating said low boiling component vapor;
  (g) means for recovering condensed low boiling component from said condenser means; and
  (h) means for removing the remainder of said liquid feed from said evaporator means.

69. A system, as claimed in claim 68, wherein said means for driving said first compressor comprises at least a part a mechanical energy source and means drivingly linking said mechanical energy source to said compressor.

70. A system, as claimed in claim 68, further including duct means upstream of said condenser means and communicating with said evaporator means for diverting a fraction of said vapor exiting said first mixing chamber directly to said evaporator means for admixture with said impure liquid feed therein.

71. A system, as claimed in claim 68, further including duct means downstream of said first compressor means for diverting a fraction of said compressed vapor directly to said means for supplying impure liquid feed to said evaporator means.

72. A system, as claimed in claim 71, wherein said means for supplying impure liquid feed includes a feed duct and said duct means downstream of said first compressor means includes a vapor injector means communicating with said feed duct to inject compressed vapor therein.

73. A system, as claimed in claim 68, including means for controlling the portion of said compressed vapor flow diverted into said by-pass duct means.

74. A system, as claimed in claim 73, wherein said by-pass duct means include by-pass arms and vapor injector means at the end of said arms remote from said first compressor means, said vapor injector means injecting said by-pass vapor into said first mixing chamber.

75. A system, as claimed in claim 68, wherein said means for supplying make-up work comprises a second mixing chamber for receiving said portion of said vapor from said first compressor means and means for supplying hot gases under pressure to said second mixing chamber, said hot gases admixing with and transferring heat directly to said vapor portion from said first compressor means in said second mixing chamber, and resulting heated vapor expanding through, doing work upon and motivating said expansion engine means.

76. A system, as claimed in claim 75, wherein said means for supplying hot gases comprises gas supply means and gas injector means, said gas injector means receiving gas from said gas supply means and injecting said gas into said second mixing chamber.

77. A system, as claimed in claim 75, wherein said expansion engine means is coaxial with said first compressor means and said second mixing chamber is disposed therebetween.

78. A system, as claimed in claim 68, wherein said condenser means is disposed within said evaporator means in heat transfer relationship with said liquid feed in said evaporator means.

79. A system, as claimed in claim 68, wherein said condenser means comprises heat exchange means disposed outside of said evaporator means.

80. A system, as claimed in claim 68, wherein said means for driving said first compressor means includes at least in part auxiliary turbine means drivingly connected to said compressor means, said auxiliary means including a conduit for gas flow therethrough and turbine blading in said conduit, said turbine blading drivingly linked to said compressor means, whereby gas flow through said conduit does work on said turbine blading which work is transmitted to said compressor means.

81. A system, as claimed in claim 68, wherein said conduit is annularly disposed with respect to and separated from the space in which said vapor flows, said compressor means is drivingly connected to said auxiliary turbine means through a shaft, and said auxiliary turbine means includes a spindle supporting said blading and drivingly connected to said shaft.

82. A system, as claimed in claim 81, wherein said auxiliary turbine spindle is hollow and said vapor flows therethrough.

83. A system, as claimed in claim 80, further including auxiliary compressor means in said conduit upstream of and drivingly connected to said auxiliary turbine means, said auxiliary compressor means drawing air through said conduit whereby said air flow together with said gas flow in said conduit motivates said auxiliary turbine means.

84. A system, as claimed in claim 81, including auxiliary compressor means disposed in said annular conduit, said auxiliary compressor means drivingly connected to said auxiliary turbine means through said shaft and including a spindle supporting compressor blading in said conduit.

85. A system, as claimed in claim 84, wherein said compressor spindle is hollow and said vapor flows through said spindle.

86. A system, as claimed in claim 68, wherein said first compressor means has a compression ratio in the range 1.2:1 to 250:1.

* * * * *